United States Patent [19]
Flach et al.

[11] Patent Number: 5,944,659
[45] Date of Patent: Aug. 31, 1999

[54] ARCHITECTURE FOR TDMA MEDICAL TELEMETRY SYSTEM

[75] Inventors: Terry E. Flach, Altadena; Michael D. Stoop, Aliso Viejo, both of Calif.

[73] Assignee: Vitalcom Inc., Tustin, Calif.

[21] Appl. No.: 08/675,594

[22] Filed: Jul. 2, 1996

Related U.S. Application Data

[60] Provisional application No. 60/006,600, Nov. 13, 1995.

[51] Int. Cl.$^6$ ........................................................ A61F 2/02
[52] U.S. Cl. ............................................ 600/300; 128/903
[58] Field of Search ..................................... 128/630, 903, 128/904, 637, 638, 670, 671, 731–733, 739–741

[56] References Cited

U.S. PATENT DOCUMENTS

| | | |
|---|---|---|
| 3,826,868 | 7/1974 | Nugent . |
| 3,925,762 | 12/1975 | Heitlinger et al. . |
| 4,051,522 | 9/1977 | Healy et al. . |
| 4,539,710 | 9/1985 | Dinsmore . |
| 4,958,645 | 9/1990 | Cadell et al. . |
| 5,153,584 | 10/1992 | Engira . |
| 5,205,294 | 4/1993 | Flach et al. . |
| 5,238,001 | 8/1993 | Gallant et al. . |
| 5,270,811 | 12/1993 | Ishibashi et al. . |
| 5,305,202 | 4/1994 | Gallant et al. . |
| 5,305,353 | 4/1994 | Weerackody . |
| 5,309,920 | 5/1994 | Gallant et al. . |
| 5,359,641 | 10/1994 | Schull et al. . |
| 5,375,604 | 12/1994 | Kelly et al. . |
| 5,381,798 | 1/1995 | Burrows . |
| 5,416,695 | 5/1995 | Stutman et al. . |
| 5,441,047 | 8/1995 | David et al. . |
| 5,458,122 | 10/1995 | Hethuin . |
| 5,458,123 | 10/1995 | Unger . |
| 5,507,035 | 4/1996 | Bantz et al. . |
| 5,579,001 | 11/1996 | Dempsey et al. . |
| 5,579,378 | 11/1996 | Arlinghaus, Jr. . |
| 5,579,775 | 12/1996 | Demspey et al. . |
| 5,614,914 | 3/1997 | Bolgiano et al. . |

FOREIGN PATENT DOCUMENTS

| | | |
|---|---|---|
| 2258960 | 2/1993 | United Kingdom . |
| 2271691 | 4/1994 | United Kingdom . |

*Primary Examiner*—Robert L. Nasser
*Attorney, Agent, or Firm*—Knobbe, Martens Olson & Bear, LLP

[57] ABSTRACT

A medical telemetry system is provided for collecting the real-time physiologic data of patients (including ambulatory patients) of a medical facility, and for transferring the data via RF to a real-time data distribution network for monitoring and display. The system includes battery-powered remote telemeters which attach to respective patients, and which collect and transmit (in data packets) the physiologic data of the patients. The remote telemeters communicate bi-directionally with a number of ceiling-mounted RF transceivers, referred to as "VCELLs," using a wireless TDMA protocol. The VCELLs, which are hardwire-connected to a LAN, forward the data packets received from the telemeters to patient monitoring stations on the LAN. The VCELLs are distributed throughout the medical facility such that different VCELLs provide coverage for different patient areas. As part of the wireless TDMA protocol, the remote telemeters continuously assess the quality of the RF links offered by different nearby VCELLs (by scanning the frequencies on which different VCELLs operate), and connect to those VCELLs which offer the best link conditions. To provide a high degree of protection against multi-path interference, each remote telemeter maintains connections with two different VCELLs at-a-time, and transmits all data packets (on different frequencies and during different timeslots) to both VCELLs; the system thereby provides space, time and frequency diversity on wireless data packet transfers from the telemeters. The telemeters and VCELLs also implement a patient location protocol for enabling the monitoring of the locations of individual patients. The architecture can accommodate a large number of patients (e.g., 500 or more) while operating within the transmission power limits of the VHF medical telemetry band.

36 Claims, 11 Drawing Sheets

TIMESLOT STATUS TABLE
900

|  | SLOT 1 | SLOT 2 | SLOT 3 | SLOT 4 | SLOT 5 | SLOT 6 |
|---|---|---|---|---|---|---|
| ASSIGNED | ✓ | ✓ |  | ✓ | ✓ |  |
| FRAMES SINCE LAST PACKET | 0 | 0 | (NA) | 3 | 0 | (NA) |

FIG. 9

VCELL CATALOG
1100

|  | RATING | CONNECTED TO | LOW-PWR. SIGNAL STRENGTH |
|---|---|---|---|
| VCELL1 (f1) | 7 |  | 1 |
| VCELL2 (f2) | 8 | ✓ | 9 |
| VCELL3 (f3) | 8 |  | 6 |
| VCELL4 (f4) | 8 | ✓ | 6 |
| VCELL5 (f5) | 6 |  | 1 |
| VCELL6 (f6) | 2 |  | 0 |
| VCELL7 (f7) | 0 |  | 0 |
| VCELL8 (f8) | 0 |  | 0 |
| VCELL9 (f9) | 3 |  | 0 |
| VCELL10 (f10) | 5 |  | 1 |

FIG. 11

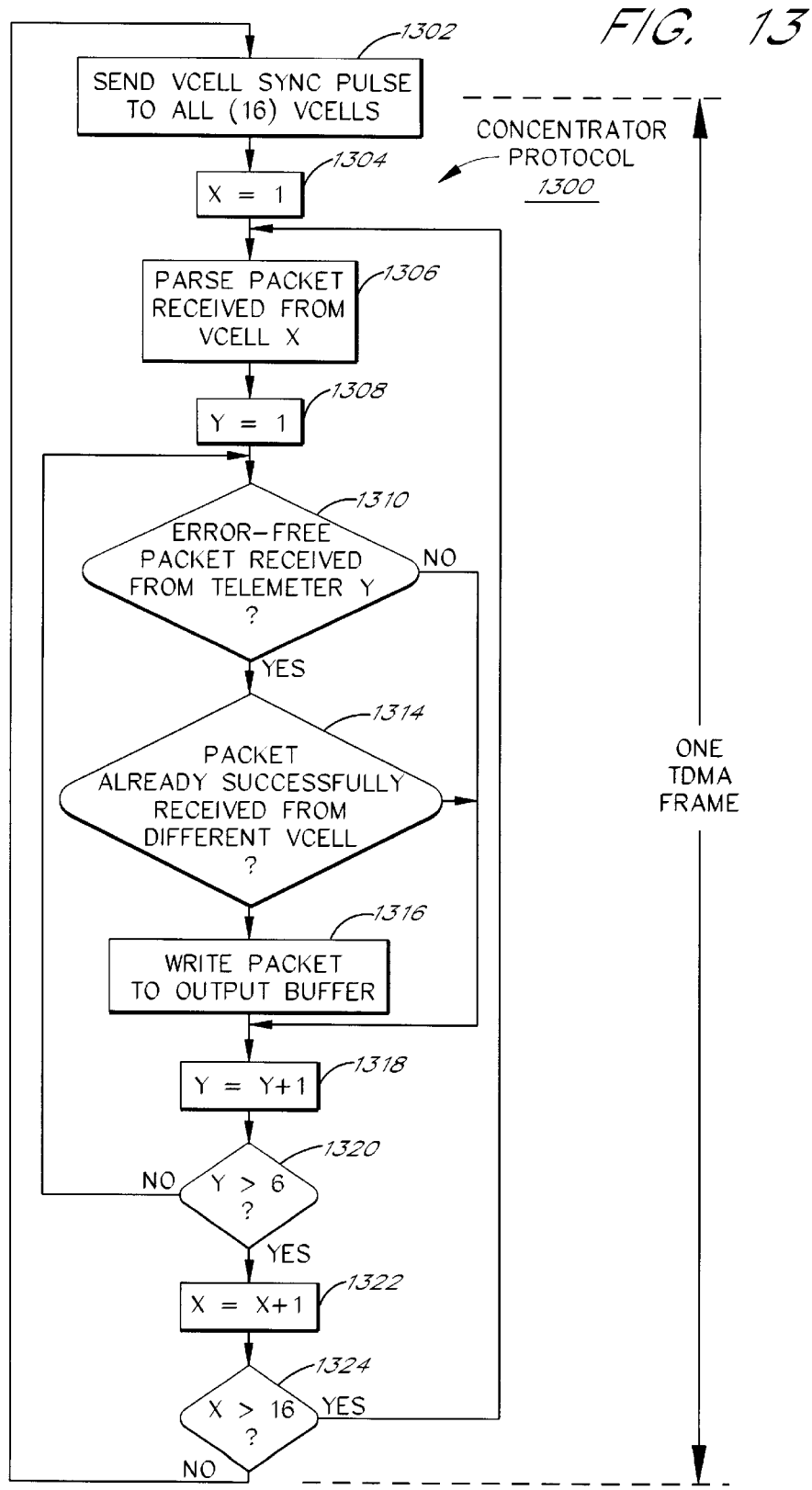

ARCHITECTURE FOR TDMA MEDICAL TELEMETRY SYSTEM

PRIORITY CLAIM

This application claims the benefit of U.S. Provisional Appl. No. 60/006,600 titled TWO-WAY TDMA TELEMETRY SYSTEM, filed Nov. 13, 1995.

BACKGROUND OF THE INVENTION

1. Field of the Invention

The present invention relates to digital wireless communications systems of the type which employ portable, battery-powered communications devices, such as remote telemeters worn by ambulatory hospital patients for monitoring purposes. More particularly, the present invention relates to a network architecture, and an associated TDMA (time division multiple access) communications protocol, for facilitating the efficient and reliable exchange of information between portable wireless devices and centralized monitoring stations.

2. Description of the Related Art

Medical telemetry systems that allow the physiologic data of multiple, remotely-located patients to be monitored from a central location are known in the art. These systems typically comprise remote telemeters that remotely collect the physiologic data of respective patients and transmit the data over a wireless link to a centralized monitoring station. This physiologic data may include, for example, real-time electrocardiograph (ECG) waveforms, $CO_2$ levels, and temperature readings. From the centralized monitoring station, a clinician can visually monitor the physiologic status, in real time, of many different patients. The central station may also run automated monitoring software for alerting the clinician whenever a predetermined physiologic event occurs, such as a cardiac arrythmia condition.

Remote telemeters of medical telemetry systems are generally of two types: instrument remote telemeters and ambulatory remote telemeters. An ambulatory remote telemeter is a portable, battery-powered device which permits the patient to be monitored while the patient is ambulatory. The ambulatory telemeter attaches to the patient by a strap or other attachment device, and receives the patient's physiologic data via ECG leads (and/or other types of sensor leads) which attach to the patient's body. The physiologic data is continuously transmitted to the central monitoring station by the telemeter's RF (radio frequency) transmitter to permit real-time monitoring. (A design of a remote transceiver which may be used in a two-way, ambulatory telemeter is described in the above-referenced provisional application.) Instrument remote telemeters operate in a similar manner, but receive the patient's physiologic data from a bedside monitor (or other instrument) over a hardwired link, such as an RS-232 connection. Instrument remote telemeters that transfer the physiologic data to the central station over a hardwired connection are also common.

SUMMARY OF THE INVENTION

One problem that is commonly encountered in the field of medical telemetry involves signal loss caused by multi-path interference. Multi-path interference is a well-known phenomenon which occurs when a signal takes two or more paths (as the result of signal reflections) from the transmitter to the receiver such that the multi-path components destructively interfere with each other at the receiver's antenna. To reduce the effects of multi-path interference, some telemetry equipment manufactures have included multiple antenna/receiver pairs on each remote telemeter. With this technique, known as spacial diversity, when one of the antennas experiences multipath fading, the other antenna (and the corresponding receiver) is used to receive the signal. One problem with this method is that it adds to the cost, size and complexity of the remote telemeter. In addition, in at least some implementations, a loss of data may occur when a "switch-over" is performed from one antenna/receiver pair to the other.

Another problem that has been encountered in the field of medical telemetry relates to the ability to monitor a large number of patients over a coverage area that extends to all patient areas of the hospital. A common solution to this problem involves installing a large number of antennas (e.g., 200 or more) throughout the hospital (with different antennas positioned in different patient areas), and interconnecting the antennas using signal combiners to form a single, distributed antenna system. One problem with this "distributed antenna system" approach is that each antenna and its associated preamplifier (or preamplifiers) contributes to the noise floor of the antenna system, and thereby increases the minimum transmit power at which the transmitting components of the system can operate. (The reasons for this noise floor degradation are discussed below.) Consequently, unless the transmission power of the system's transmitters is increased, a practical limitation is imposed on the number of antennas that can be included in the system, and on the coverage area provided by the system.

Although the noise floor degradation problem can potentially be overcome by increasing the transmission power of the telemetry equipment, there are at least two problems associated with increasing the transmit power. The first problem is that under existing Federal Communications Commission (FCC) regulations, medical telemetry equipment is only permitted to operate within certain frequency bands, and must operate within certain prescribed power limits within these bands. Under FCC Part 15.241, for example, which governs the protected VHF (174–216 MHz) medical telemetry band (a band which is generally restricted to VHF television and medical telemetry), telemetry devices are not permitted to transmit at a signal level which exceeds 1500 microvolts/meter at 3 meters. To operate at power levels which exceed this maximum, frequency bands which offer less protection against interference must be used. The second problem is that increasing the transmit power of an ambulatory telemeter will normally produce a corresponding reduction in the telemeter's battery life.

Another problem with distributed antenna systems is that they are typically highly vulnerable to isolated sources of electromagnetic interference ("EMI"). Specifically, because the signals received by all of the antennas are combined using RF signal combiners, a single source of interference (such as a cellular phone or a faulty preamplifier) at or near one of the antennas can introduce an intolerable level of noise into the system, potentially preventing the monitoring of all patients. One consequence of this problem is that antennas generally cannot be positioned near known intermittent sources of EMI such as X-ray machines, CAT (computerized axial tomography) scanners, and fluoroscopy machines, preventing patient monitoring in corresponding diagnostic areas.

In light of these and other problems with existing medical telemetry systems, the present invention seeks to achieve a number of performance-related objectives. One such objective is to provide an architecture in which the coverage area and patient capacity can be increased without degrading the noise floor. This would allow the telemetry system to be expanded in size and capacity without the need to increase the transmit power of the battery-powered remote telemeters, and without the need to operate outside the protected VHF medical telemetry band. A related objective is to provide an architecture which is highly scalable, so that the capacity and coverage area of the system can easily be expanded through time.

Another goal of the invention is to provide extensive protection against signal drop-outs caused by multi-path interference. The present invention seeks to achieve this objective without the need for multiple antennas or receivers on the telemeters, and without the loss or interruption of physiologic data commonly caused by antenna/receiver switch-overs. A related goal is to provide a high degree of protection against isolated sources of EMI, and to allow patients to be remotely monitored while near known intermittent sources of interference.

Another goal of the invention is to provide an architecture in which a large number of patients (e.g., 500 to 800 or more) can be monitored using a relatively narrow range of RF frequencies (such as the equivalent of one or two VHF television channels). This would allow the RF communications components of the system to be optimized for narrow-band operation, which would in-turn provide a performance advantage over wide-band systems.

In accordance with these and other objectives, a medical telemetry system is provided which includes multiple remote telemeters (which may include both ambulatory and instrument telemeters) which transmit the real-time physiologic data of respective patients via RF to multiple ceiling-mounted transceivers, referred to as "VCELLs." The VCELLs are hardwire-connected to a real-time data distribution network which includes at least one centralized monitoring station. (In a preferred implementation, each group of 16 VCELLs is connected via twisted pair lines to a respective "concentrator PC," and the concentrator PCs and monitoring stations are interconnected as part of a hospital local area network.)

The VCELLs are distributed throughout the hospital such that different VCELLs provide coverage for different patient areas, and are spaced such that the coverage zones provided by adjacent VCELLs overlap with one another. Different VCELLs within the same general area communicate with the remote telemeters on different respective RF frequencies (i.e., frequency channels), so that a remote telemeter can selectively communicate with a given VCELL by selecting that VCELL's frequency. As described below, however, VCELL frequencies are reused by VCELLs that are spaced sufficiently apart from one another to avoid interference, allowing the system to be implemented as a narrow-band system which uses a relatively small number of frequencies (e.g., 10) to provide coverage for an entire hospital facility.

In a preferred embodiment, the remote telemeters communicate with the VCELLs using a wireless time division multiple access (TDMA) protocol in which each VCELL can concurrently receive the real-time physiologic data of up to six remote telemeters (corresponding to six patients). As part of this protocol, the remote telemeters implement a VCELL "switch-over" protocol in which the telemeters establish wireless connections with different VCELLs based on periodic assessments (made by the telemeters) of the wireless links offered by the different VCELLs. Thus, as a patient moves throughout the hospital, the patient's remote telemeter may connect to (and disconnect from) many different VCELLs.

In operation, the remote telemeters send data packets (during assigned timeslots) to the respective VCELLs with which the telemeters have established wireless connections. (As described below, each remote telemeter preferably remains connected to two different VCELLs at-a-time to provide extensive protection against multi-path interference.) These data packets include the real-time physiologic data of respective patients, and include ID codes which identify the remote telemeters. The VCELLs in-turn forward the data packets to the real-time data distribution network to permit the real-time monitoring of the patients of the system.

To provide protection against multi-path interference and other causes of data loss, each remote telemeter maintains wireless connections with two different VCELLs at-a-time, and transmits each data packet to both of the VCELLs. These duplicate packet transmissions to the two different VCELLs take place on different frequencies during different TDMA timeslots. The two VCELLs forward the data packets to a centralized node (which may be a monitoring station or a concentrator PC in the preferred embodiment), which performs error correction by selecting between the corresponding packets based on error detection codes contained within the packets. Thus, the patient's physiologic data is sent from the remote telemeter to the centralized node over two separate data paths. Because the two VCELLs are spaced apart, and because the duplicate packets are transferred to the VCELLs on separate frequencies at different times, the packet transfers benefit from the protection offered by spacial diversity, frequency diversity and time diversity.

The architecture of the above-described medical telemetry system provides numerous advantages over prior art systems. One such advantage is that the system can be expanded in patient capacity and coverage area, by the addition of VCELLs, without increasing the noise floor of the system beyond the natural thermal noise floor. (This is because the data signals received by the VCELLs are multiplexed digitally at baseband, rather than being combined by RF analog signal combiners.) Thus, unlike distributed antenna telemetry systems, the noise floor does not impose an upper limit on the size of the system. Moreover, the architecture can accommodate a large number of patients (e.g., 500 to 800 or more) using a low maximum transmission power, such as the maximum transmit power permitted by the FCC for operation within the VHF medical telemetry band.

Another advantage is that the architecture is highly immune to isolated sources of EMI. A source of EMI (such as a cellular phone), for example, will typically contaminate the signals received by no more than one or two nearby VCELLs, as opposed to introducing noise into the entire system. (Because the remote telemeters connect to two VCELLs at-a-time, and automatically switch to different VCELLs when bad link conditions are detected, the contamination of one or two VCELLs will typically result in little or no loss of telemetry data.) One benefit of this immunity is that VCELLs can be installed within X-ray rooms and other radiological diagnostic rooms which contain intermittent sources of EMI, allowing patients to be monitored in such areas.

Another advantage of the architecture is that it permits the reuse of RF frequencies by VCELLs that are sufficiently spaced apart (by about 500 feet in a VHF implementation) to avoid interference with each other. By extending this concept, the present invention provides coverage for the entire facility using a relatively small number of frequencies which fall within a relatively narrow frequency band. In a preferred VHF implementation, for example, it is estimated that a typical hospital can be covered using only 10 to 12 VCELL frequencies which fall within a frequency band that is equal in width to about two adjacent VHF television channels. This characteristic of the architecture advantageously allows the telemeter transceivers to be optimized (through the appropriate selection of transceiver components) for a relatively narrow band of frequencies, which in-turn improves performance.

BRIEF DESCRIPTION OF THE DRAWINGS

These and other features of the invention are described below with reference to the drawings of a preferred embodiment, which is intended to illustrate and not to limit the invention:

FIG. 9 illustrates the basic timeslot status information stored by each VCELL as part of the wireless TDMA protocol.

FIG. 11 illustrates the basic VCELL status information stored by each remote telemeter as part of the wireless TDMA protocol.

FIG. 13 is a flow chart of a protocol followed by the concentrators PCs for processing packets received from the VCELLs.

Figure 1:
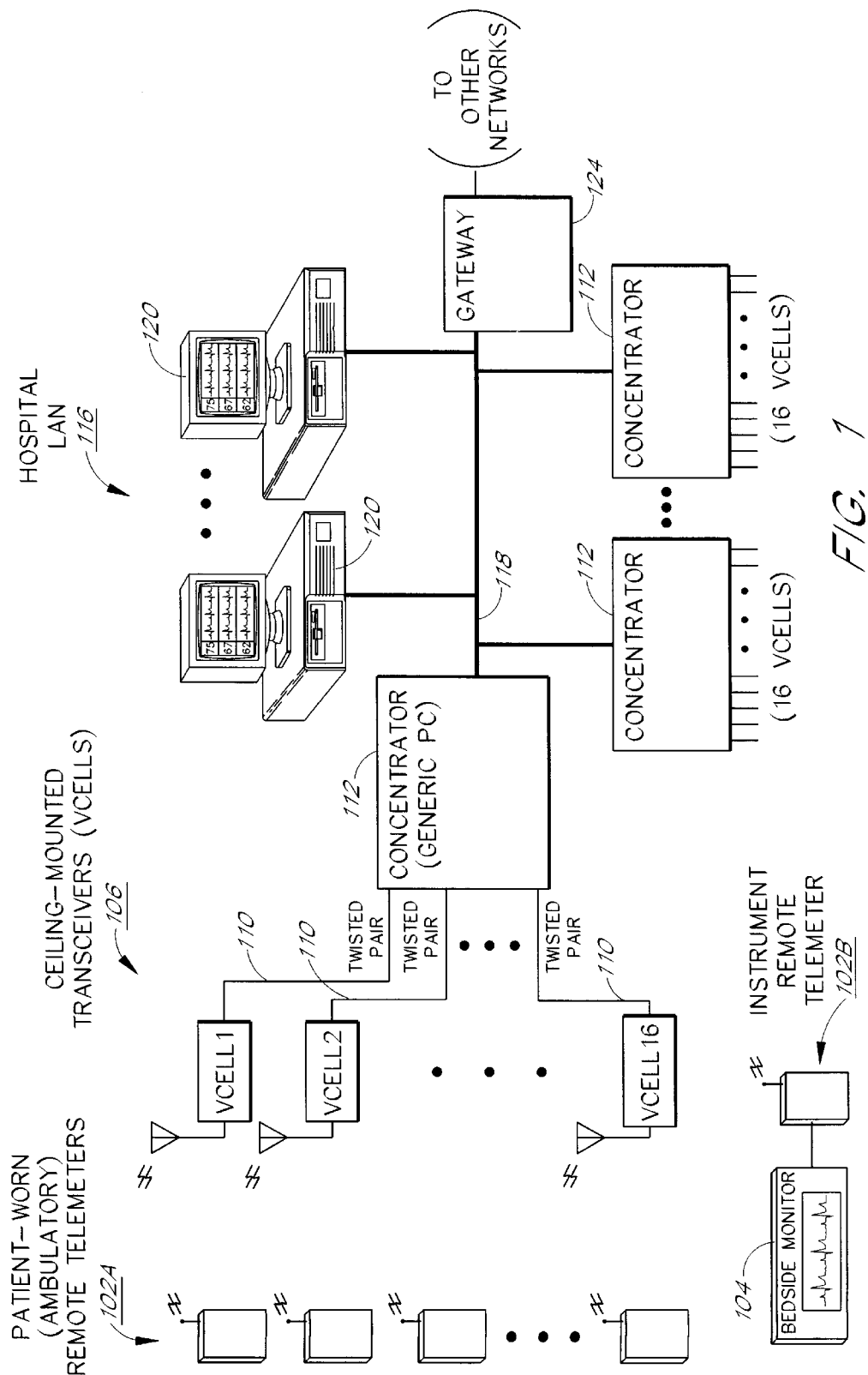
FIG. 1 is an architectural drawing of the hardware components of a medical telemetry system in accordance with the present invention.

In the drawings, the left-most digit (or digits) of each reference number indicates the figure in which the item first appears. For example, an element with the reference number 310 first appears in FIG. 3, and an element with reference number 1100 first appears in FIG. 11.

DETAILED DESCRIPTION OF THE PREFERRED EMBODIMENTS

To facilitate a complete understanding of the invention, the description of the preferred embodiment is arranged within the following sections and subsections:

1. OVERVIEW
   (i) GENERAL OPERATION
   (ii) HARDWARE COMPONENTS
   (iii) PATIENT CAPACITY AND DATA THROUGHPUT
   (iv) NOISE FLOOR IMPROVEMENT
   (v) PROTECTION AGAINST ISOLATED EMI SOURCES
   (vi) VCELL SPACING AND FREQUENCY REUSE
2. COMMUNICATIONS BETWEEN REMOTE TELEMETERS AND VCELLS
   (i) OVERALL WIRELESS TDMA PROTOCOL
   (ii) VCELL PROTOCOL
   (iii) REMOTE TELEMETER PROTOCOL
3. COMMUNICATIONS BETWEEN VCELLS AND CONCENTRATORS
   (i) PROCESSING OF TELEMETER COMMANDS
4. DATA TRANSFERS OVER LAN
5. VCELL LOAD MONITORING
6. TRANSCEIVER CIRCUIT AND OPERATION
7. CONCLUSION 1. Overview (FIGS. 1–7)

Figure 2:
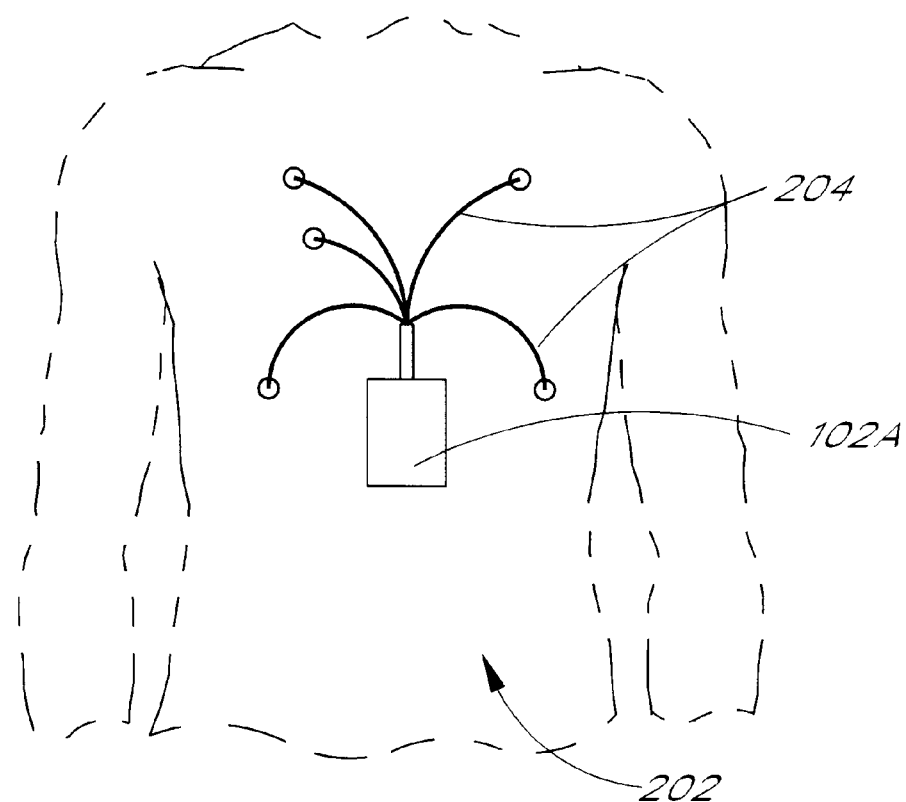
FIG. 2 illustrates the attachment of an ambulatory remote telemeter to a patient of the system.

FIG. 1 illustrates the general architecture of a two-way medical telemetry system which operates in accordance with the present invention. The system, referred to herein as the "VCELL system," includes a number of wireless remote telemeters 102A, 102B which collect, packetize and transmit the physiologic data of respective hospital patients. (As used herein, the term "wireless" means that data is transferred to and/or from the device over a wireless medium.) The remote telemeters 102 may include both patient-worn (ambulatory) remote telemeters 102A which connect directly to the patient (as generally illustrated in FIG. 2), and instrument remote telemeters 102B which connect to a bedside or other patient monitor 104. The physiologic data transmitted by the remote telemeters may include, for example, real-time ECG signals, blood pressure readings, $CO_2$ levels, and temperature readings. The remote telemeters 102 may additionally sense and transmit various types of non-physiologic data, such as battery-level status data, ECG loose-lead status data, and patient location data. (The term "patient data" is used herein to refer collectively to the physiologic and non-physiologic data captured by the remote telemeters 102.)

The remote telemeters 102 communicate bi-directionally with a number of ceiling-mounted radio transceivers 106, referred to as "VCELLS," using a time division multiple access (TDMA) protocol. In one mode of operation, each VCELL 106 can communicate with up to six remote telemeters 102 at-a-time at a rate of 10 kilobaud (Kbaud) per telemeter. The VCELLs 106 are spaced apart from one another (typically by about 50 to 75 feet, depending upon expected patient density) throughout the hospital to provide a "cell-like" coverage area which consists of overlapping zones of coverage.

Different VCELLs 106 of the system operate (i.e., transmit and receive data) on a different RF frequency channels ("frequencies") within the VHF medical telemetry band (174–216 MHz). However, VCELLs that are sufficiently spaced apart to avoid interference with one another may operate on like frequencies, as described below. The VCELLs 106 and telemeters 102 of the preferred embodiment operate in compliance with the spectrum utilization and transmission power limitations of FCC Part 15.241. Although the system preferably operates within the VHF medical telemetry band, other suitable frequency bands may be used. In addition, although the system uses frequency division multiplexing to separate the data transmissions to and from different VCELLs 106, other channel separation techniques can be used.

Although the remote telemeters 102 and VCELLs 106 shown in FIG. 1 are of the type which communicate by radio frequency (RF), the system may also include "hardwired" remote telemeters and VCELLs which communicate over hardwire connections. For purposes of this description, however, it may be assumed that the terms "remote telemeter" and "VCELL" refer to RF devices, except where indicated otherwise.

With further reference to FIG. 1, the VCELLs 106 are connected by conventional shielded twisted pair lines 110 to concentrator PCs 112 ("concentrators"). In the preferred embodiment, each concentrator 112 can accommodate up to sixteen VCELLs 106. In a typical hospital installation, one concentrator 112 will service a single floor of the hospital. The concentrators 112 provide connectivity between the VCELLs 106 an a hospital local area network (LAN) 116. The LAN 116 serves as a real-time data distribution system for distributing the physiologic data of the patients with a known latency. The LAN 116 includes a 100 Mbit/second backbone 118 which is based on the 100BaseTx (Ethernet) protocol. (The term "backbone" refers generally to the transmission medium and the networking cards of the LAN.) Alternative LAN protocols which could be used include ATM (Asynchronous Transfer Mode) and FDDI (Fiber Distributed Data Interface) and others.

The LAN 116 includes multiple monitoring stations 120 for allowing hospital personnel to remotely view and otherwise monitor the real-time physiologic data of the patients of the system. Each monitoring station 120 is preferably in the form of a standard 486 or Pentium based PC (personal computer) which runs conventional patient monitoring software, such as the VCOM (MPC 1100) patient monitoring software package available from VitalCom Incorporated. The patient monitoring software can also be loaded onto the concentrator PCs 112 so that the concentrators double as monitoring stations. The LAN 116 may also include one or more gateway computers 124 for connecting the LAN 116 to other networks, such as the Internet, to permit the exchange of patient information with other medical facilities and patient sites.

As will be apparent, the architecture illustrated in FIG. 1 provides for a high degree of scalability. The system can initially be installed, for example, as a single concentrator PC 112 which serves as the sole monitoring station for a set of 16 (or fewer) VCELLs, which may include both RF and hardwired VCELLs. With the addition of a LAN, new VCELLs 106 and concentrators 112 can be added to increase the patient capacity and/or coverage area of the system. (As described below, the architecture allows new VCELLs to be added to the system without a corresponding degradation in performance caused by noise.) Monitoring stations 120 can be added to the LAN 116 as needed to permit the remote viewing and monitoring of patient data from various locations within the hospital.

(i) General Operation

In operation, the remote telemeters 102 send data packets to individual VCELLs 106 using a wireless TDMA protocol. These packets include the patient data collected by the remote telemeters 102 (or by patient monitors connected to the remote telemeters), along with the ID codes of the respective telemeters 102. The VCELLs 106 forward these data packets to the corresponding concentrators 112, which in-turn broadcast the patient data on the LAN 116 (in real time) for viewing and automated monitoring by the monitoring stations 120. The wireless TDMA protocol includes control timeslots for allowing the VCELLs to pass control information (e.g., synchronization information, commands, and timeslot assignments) to the remote telemeters 102. In addition, the protocol supports a patient location method (described below) for monitoring the remote location of each patient.

To support patient mobility, the VCELLs 106 and remote telemeters 102 implement a "switch-over" protocol in which the telemeters 102 continuously attempt to establish connections with those VCELLs which offer the best link performance. As part of this protocol, each remote telemeter continuously assesses the quality of the RF link to each VCELL that is within range. The telemeters store this link assessment information within respective VCELL "catalogs" (described below), and periodically evaluate these catalogs to determine whether a switch-over to a new VCELL is desirable. When a remote telemeter 102 determines that a VCELL is available (i.e., has an open timeslot) which offers better link performance than a current VCELL (i.e., a VCELL to which the telemeter is currently connected), the remote telemeter attempts to connect to the new VCELL. (As described below, this involves sending a timeslot request message to the selected VCELL 106, and then waiting for confirmation message from the VCELL.) If the connection is successfully established, the remote telemeter 102 drops its connection to the current VCELL 106. Thus, a remote telemeter 102 will normally connect to many different VCELLs 106 (including VCELLs of different concentrators 112) as the patient moves throughout the hospital. Transitions between VCELLs occur without interruption or loss of data, and are thus seamless from the viewpoint of the monitoring clinician.

To provide protection against dropouts caused by multipath interference (and other types of interference), each remote telemeter 102 attempts to maintain a connection with two VCELLs 106 at all times. (In other implementations, the remote telemeters 102 may connect to three or more VCELLs 106 to provide even greater protection against multi-path interference.) Whenever two VCELL connections are established, the remote telemeter 102 transmits each of its data packets to both of the VCELLs. These redundant transfers take place on different frequencies during different TDMA timeslots. Thus, each wireless data path benefits from the protection offered by space, time, and frequency diversity. Upon receiving the redundant packets, the concentrator 112 to which the two VCELLs 106 are connected (assuming the VCELLs are connected to the same concentrator) uses error detection codes contained within the packets to discard bad packets, and to discard duplicate packets when both packets are successfully received.

In one implementation of the system, the remote telemeters 102 can only connect to the VCELLs 106 of one concentrator 112 at-a-time. In this implementation, each remote telemeter 102 attempts to stay connected to the VCELLs of the current concentrator 112, and switches over to a different concentrator only when deemed necessary. In another implementation, the concentrators 112 of the system are maintained sufficiently synchronized with one another to allow each remote telemeter to connect to VCELLs of two different concentrators 112. When this situation occurs, the task of discarding duplicate packets automatically shifts to the monitoring stations 120.

The operation of the system is described in further detail in the following sections.

(ii) Hardware Components (FIGS. 3–5A)

Figure 3:
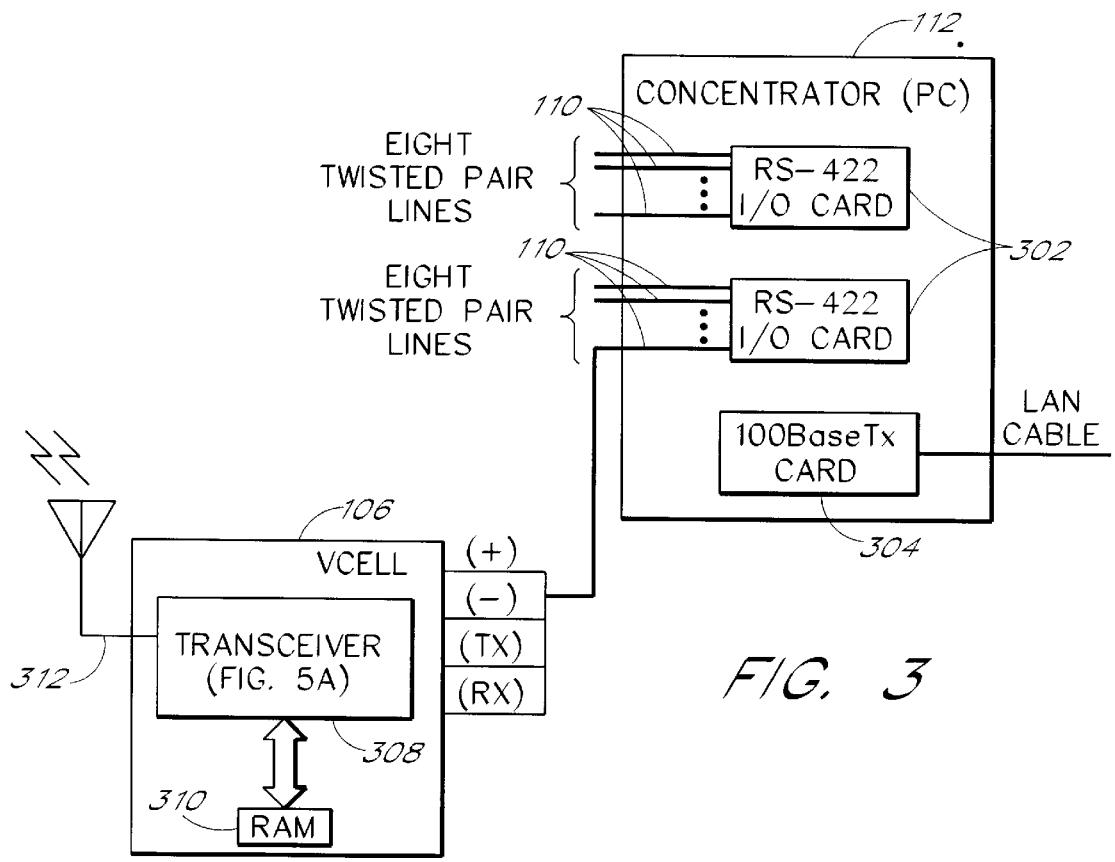
FIG. 3 illustrates the basic hardware components of the concentrator PCs and the ceiling-mounted transceivers (VCELLs) of FIG. 1.

FIG. 3 illustrates the basic components of the concentrators 112 and VCELLs 106 of the system. Each concentrator 112 comprises a generic PC having two RS-422 input-output (I/O) cards 302 and a 100BaseTx LAN card 304. The PC may, for example, be a Pentium-based PC with 16 megabytes of memory. (Additional memory and a display monitor will normally be provided if the concentrator 112 is to double as a monitoring station.) The RS-422 and 100BaseTx cards 302, 304 are standard AT size components which can be purchased off-the-shelf at computer stores.

Each RS-422 card 302 includes eight external (full duplex) I/Os which connect, respectively, to eight standard twisted pair lines 110. Each twisted pair line 110 connects to a respective VCELL 106. The twisted pair lines 110 are preferably shielded 140 Kbaud lines with RJ-45 connectors. As is conventional, each twisted pair line includes four wires: a transmit (TX) wire, a receive (RX) wire, a positive voltage (+) wire, and a negative voltage (−) wire. The (+) and (−) wires are used to provide power to the VCELLs 106, and the (RX) and (TX) wires are used for the transfer of data.

Figures 5A, 5B:
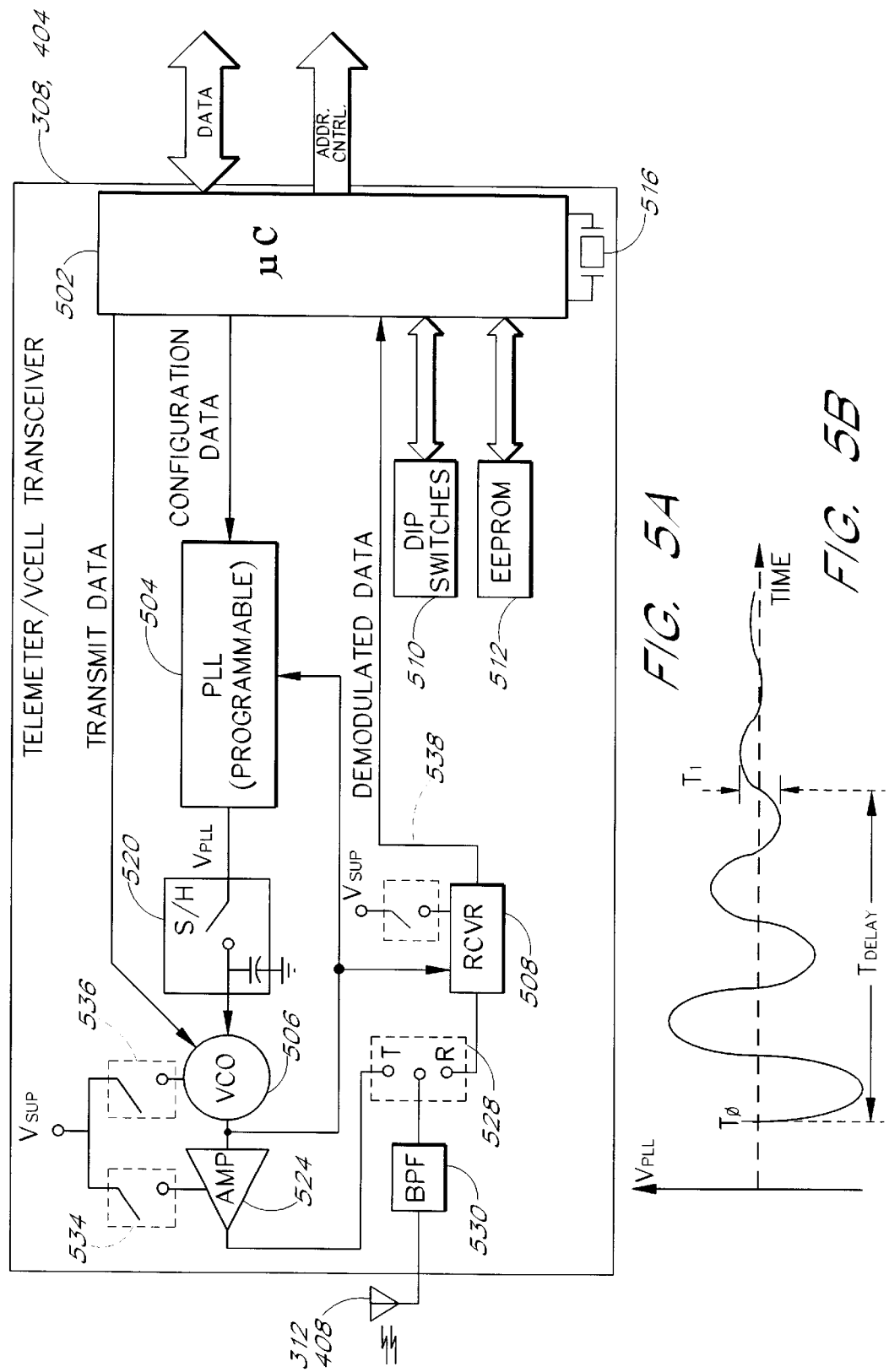
FIG. 5A is a generalized circuit diagram of a transceiver which may be used in the VCELLs and remote telemeters of the telemetry system.
FIG. 5B illustrates the output of the phase-locked loop (PLL) chip of FIG. 5A during the locking of the transmit frequency of a remote telemeter.

Each VCELL 106 is in the form of a microcontroller-based transceiver 308 coupled to an antenna 312. The specifications of a transceiver which may be used in the preferred embodiment are listed in Table 1. (A transceiver circuit which may be used within the VCELLs is illustrated in FIG. 5A, and is described below.) The transceiver 308 is coupled to random access memory (RAM) 310 for buffering packet data and storing various status information.

TABLE 1

VCELL TRANSCEIVER SPECIFICATIONS

| | |
|---|---|
| Operating Frequency | 204–216 MHz |
| Frequency Tuning | 100 KHz |
| Transmit Power | 1500 μV/meter @ 3 meters |
| Modulation Type | FSK |
| Modulation Rate | 80 Kbaud |
| Deviation | ±50 KHz |
| Receive Sensitivity | −90 dBm (BER < .001) |
| Tx/Rx Switching Time | <10 μs |
| Antenna | 1/2 Wave Turnstile |
| Power Supply | 6 to 12 VDC, <100 ma |

Figure 4:
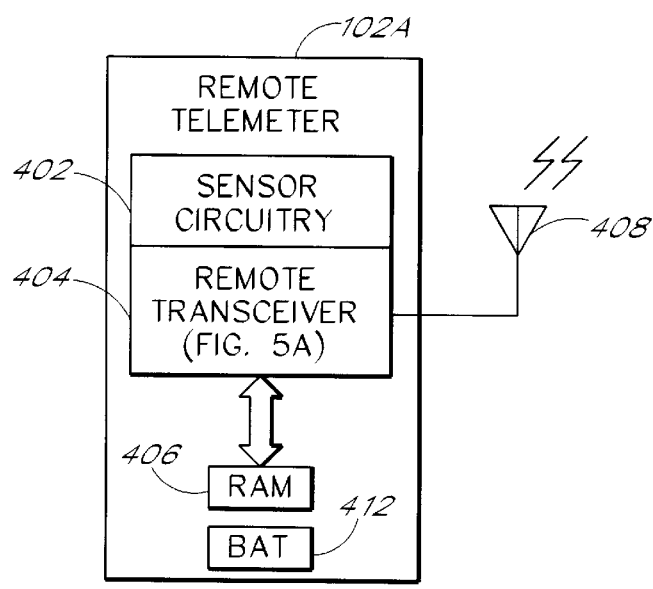
FIG. 4 illustrates the basic hardware components of the ambulatory remote telemeters of FIG. 1.

As depicted in FIG. 4, each remote telemeter 102A includes conventional sensor circuitry 402 for sensing and digitizing the patient data of a respective patient. (In instrument remote telemeters 102B of the type shown in FIG. 1, the sensor circuitry normally resides primarily within the patient monitor 104.) The sensor circuitry 402 is coupled to a microcontroller-based remote transceiver 404, which is in-turn coupled to a RAM 406 and an antenna 408. The sensor circuitry 402, remote transceiver 404 and RAM 406 are powered by one or more batteries 412. The specifications of a remote transceiver 404 which may be used in the preferred embodiment are listed in Table 2.

TABLE 2

REMOTE TELEMETER
TRANSCEIVER SPECIFICATIONS

| | |
|---|---|
| Operating Frequency | 204–216 MHz |
| Frequency Tuning | 100 KHz |
| Transmit Power | 1500 μV/meter @ 3 meters |
| Modulation Type | FSK |
| Deviation | ±50 KHz |
| Modulation Rate | 80 Kbaud |
| Receive Sensitivity | −90 dBm (BER < .001) |
| Tx/Rx Switching Time | <10 μs |
| Antenna | 1/2 Wave Turnstile |
| Power Supply | 2 Alkaline Batteries, <25 ma |

Although the architecture of FIG. 1 is not tied to any particular transceiver implementation, the remote transceiver circuit disclosed in the above-referenced provisional application (diagram reproduced as FIG. 5A) is well-suited for use as both the VCELL transceiver 308 and the remote transceiver 404. With reference briefly to FIG. 5A, the circuit includes a microcontroller 502 (preferably a 17C42) coupled to an EEPROM 512 which includes a firmware program stored therein. In the remote telemeters 102, the firmware program implements the remote telemeter side of the wireless TDMA protocol (described below). Likewise, in the VCELLs 106, the firmware program implements the VCELL side of the wireless TDMA protocol (also described below). An overview of the transceiver circuit of FIG. 5A is provided below under the heading TRANSCEIVER CIRCUIT AND OPERATION.

(iii) Patient Capacity and Data Throughput

Each VCELL 106 can receive the patient data of six patients (i.e., six remote telemeters 102) at a sustained maximum data rate of 10 Kbaud per patient. (This data rate corresponds to one timeslot per TDMA frame using a simple FM transmitter, as described below.) In addition, the architecture supports increased data rates at the expense of reduced patient capacity. For example, a VCELL 106 could receive the patient data of three patients (i.e., three remote telemeters 102) at a data rate of 20 Kbaud per patient.

The total patient capacity of the system is limited primarily by the throughput of the LAN 116. In the preferred embodiment, the system design supports approximately 900 patients at a data rate of 10 Kbaud per patient 102. This results in a backbone throughput requirement of 900×10 Kbaud=9 megabaud (Mbaud) at the network level. The use of 100BaseTx for the backbone supports this data rate while providing a margin of over 90% for overhead processing (such as synchronization, signaling, and background status keeping tasks). The patient capacity of the system can be increased by adding a second backbone 118 to the LAN 116 to provide dual 100 Mbaud data paths.

Figure 6:
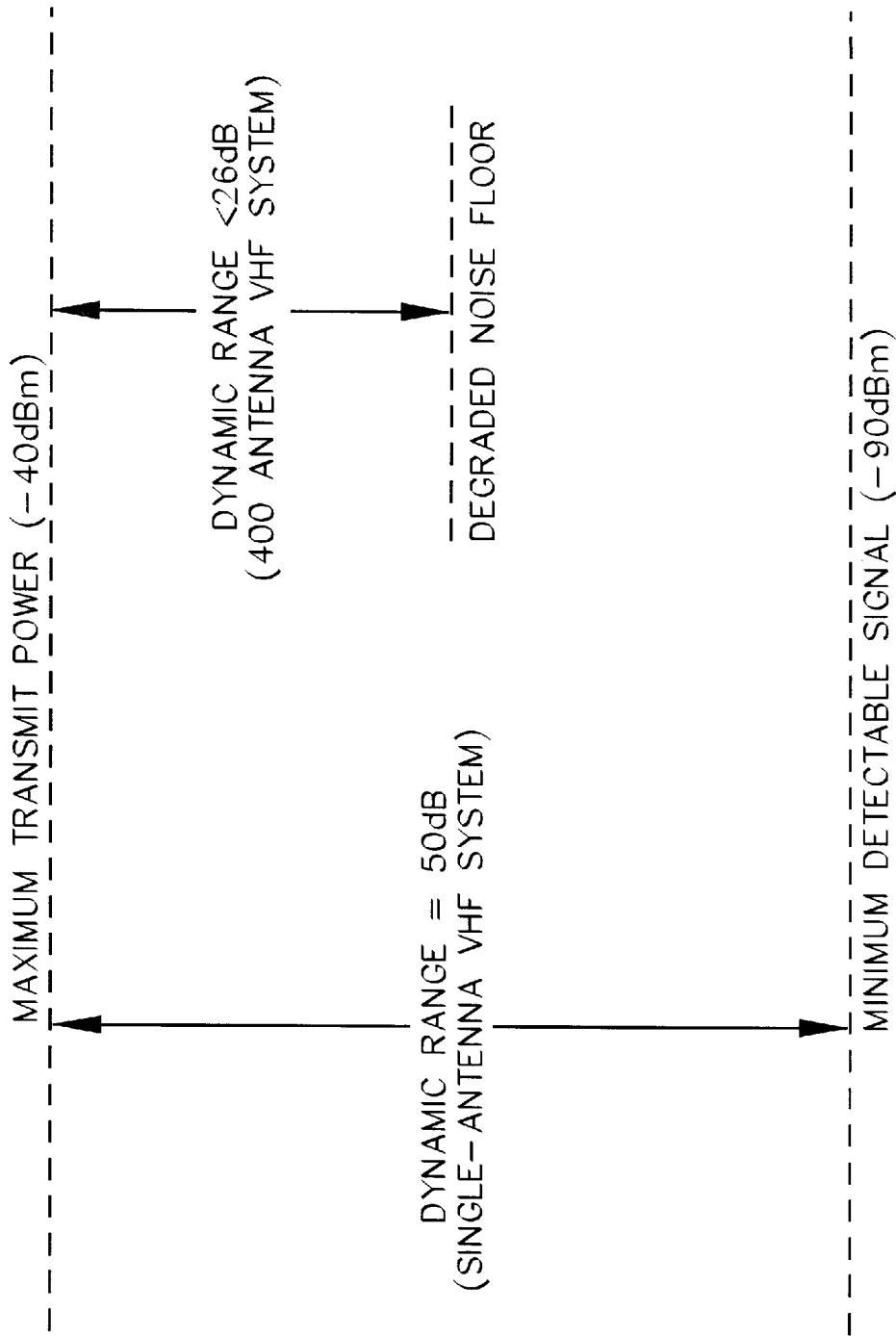
FIG. 6 illustrates an increase in dynamic range achieved by the present system over prior art telemetry systems.

(iv) Noise Floor Improvement (FIG. 6)

One significant benefit of the VCELL architecture is that it overcomes the above-described noise-floor degradation problem encountered with distributed antenna systems, and thus allows the system to be expanded in capacity (through the addition of VCELLs) without a corresponding reduction is signal quality. To illustrate the noise-floor degradation problem encountered with distributed antenna systems, reference will be made to FIG. 6, which illustrates example dynamic range values for a single-antenna system (left-hand side) and a 400 antenna system with preamplifiers (right-hand side) operating within the VHF medical telemetry band.

In general, telemetry systems operate between two limits of transmitted signal strength: (i) the minimum signal that the receiver can detect above the thermal noise floor (which is the "natural" noise floor created by the normal movement of charged particles), and (ii) the maximum signal that the transmitter can provide at very close range (as experienced when the transmitter resides directly below the receiver's antenna.) As illustrated in FIG. 6, the minimum detectable signal level (based on the thermal noise floor) in the single-antenna telemetry system will typically be about −90 dBm. The maximum allowed signal level within the VHF medical telemetry band is 1500 microvolts/meter at 3 meters (as specified by FCC Part 15.241), which corresponds to a signal level of about −40 dBm with the transmitter located directly below a ceiling-mounted telemetry antenna. Thus, a single-antenna medical telemetry system will have a dynamic range of about 50 dB.

As indicated above, the process of combining the RF signals of the antennas of a distributed antenna system has a loss associated with it. This loss results from the need for signal combiners, and from the large amount of coaxial cable required to interconnect the various antennas. To compensate for this loss, distributed antenna systems use preamplifiers, typically at the antenna sites, to boost the RF signal. One problem with this approach is that each preamplifier contributes to the noise level of the antenna system in excess of the noise actually received by the corresponding antenna. Thus, although only a few of the antennas typically receive a usable signal of a particular telemeter at any given time, all of the antennas (preamplifiers) contribute to the noise floor.

Consequently, each time the number of antennas of the distributed-antenna system is doubled, the minimum detectable signal level increases by about a factor of 2, or 3 dB. Thus, for example, a system with 400 antennas and 400 preamplifiers will suffer from a noise floor degradation of more than 24 dB (corresponding to over 8 doublings of the noise floor), producing a degraded dynamic range of less than 26 dB (FIG. 6). (A distributed antenna system of this size is currently installed at Barnes Hospital in St. Louis.) To reclaim this lost dynamic range, the remote telemeters could potentially be operated at a higher transmission power. However, the use of a higher transmission power would reduce the average battery life of remote telemeters. Moreover, an increase in power beyond the limits imposed by FCC Part 15.241 would require operation outside the protected medical telemetry band, exposing the system to new forms of RF interference.

In contrast to distributed antenna systems, the VCELL system combines the outputs of the VCELLS at baseband using digital multiplexing techniques. As a result, virtually no degradation of the noise floor occurs as VCELLs are added to the system, and the system enjoys the full 50 dB dynamic range regardless of the number of VCELLs. This has the effect of increasing the perceived transmitted power by about 24 dB (a 200 fold increase) over the 400 antenna system in the example above.

(v) Protection Against Isolated EMI Sources

Another benefit of the VCELL architecture is that it inherently offers a high degree of immunity against isolated sources of EMI (electromagnetic interference). In the above-described distributed antenna system, a single source of interference (such as an X-ray machine or a faulty copying machine) near one of the antennas can introduce an intolerable level of noise to the entire system, and prevent the monitoring of all patients of the system. In contrast, in the VCELL system, the interference source will only effect the operation of the VCELLs 106 that are sufficiently close to the source. Moreover, the contamination of one or two VCELLs by an isolated interference source will often have little or no impact on the ability to monitor patients in the area, since each remote telemeter 102 normally maintains data connections to two VCELLs 106, and automatically connects to a new VCELL source when a drop in the quality of a VCELL link is detected.

One benefit of this interference immunity is that it allows patients to be monitored near known intermittent sources of interference. For example, patients can be monitored within x-ray, fluoroscopy, and CAT-scan rooms by simply placing VCELLs in these areas.

Figure 7:
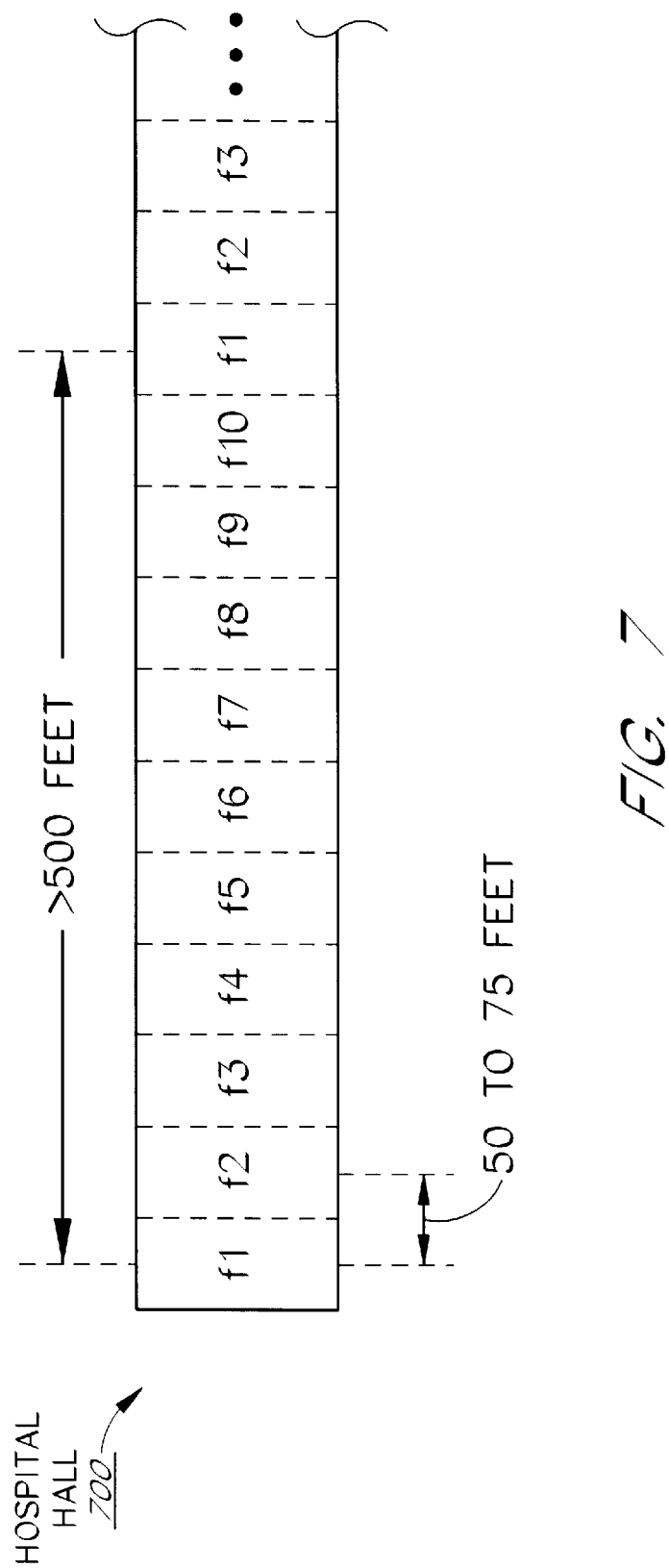
FIG. 7 illustrates how VCELLs operating on different frequencies may be arranged within a hospital hallway in accordance with the invention.

(vi) VCELL Spacing and Frequency Reuse (FIG. 7)

The VCELLs are preferably mounted sufficiently close to one another such that each patient of the system will normally be within range of multiple VCELLs 106 at any given time. (For operation at maximum power within the VHF medical telemetry band, spacings of 50 to 75 feet are suitable.) Such an arrangement allows the remote telemeters 102 to maintain connections with two VCELLs at-a-time, as is desirable for mitigating the effects of multi-path interference.

One benefit of the architecture, however, is that it allows the VCELLs to be spaced as closely together as necessary to accommodate different patient densities. For example, a relatively large number of VCELLs (each operating on a different frequency) can be placed within a hospital cafeteria to accommodate the high patient densities which may occur during meal times. Because the remote telemeters 102 only attempt to connect to the VCELLs 106 that have open timeslots (as described below), the telemetry load during such high-density events is automatically distributed among the VCELLs.

Although it is possible to configure the system such that every VCELL 106 operates (i.e., transmits and receives data) on its own unique frequency, considerable performance benefits (described below) can be realized by re-using the same set of frequencies in different regions of the hospital. In general, two VCELLs can operate on the same frequency provided that they are sufficiently spaced apart to avoid interference with one another. For operation within the VHF medical telemetry band (at the maximum allowed signal strength), a separation of 500 feet between such VCELLS is more than adequate. By assigning like frequencies during the installation process to VCELLS that are spaced 500 feet (or greater) apart, it is estimated that 10 to 12 frequencies will be sufficient to provide coverage for a typical hospital.

FIG. 7 illustrates how a set of ten frequencies can be re-used in different sections of a hospital hall 700. As illustrated, a set of ten frequencies, θ1–θ10, can be used to cover a 500 foot section of the hall using ten corresponding VCELLs. (Each frequency symbol in FIG. 7 represents one VCELL.) The same ten frequencies can then be used to cover the next 500 foot section of the hallway. With appropriate staggering of frequencies between hospital floors, the same 10 frequencies can be used to provide coverage of an entire multi-floor hospital. (While ten frequencies may be adequate for many installations, the actual number of frequencies will depend upon such factors as the hospital floor plan, the telemeter transmission power, and the expected patient densities in the various patient areas.)

The ability to reuse frequencies provides several advantages over conventional frequency division multiplexed systems. One advantage is that a reduced number of clear frequencies need to be identified during the installation process. Another advantage is that the transmitters, receivers and antennas of the system can be optimized to operate over a much narrower band of frequencies. For a system which operates within the VHF medical telemetry band, for example, the VCELL frequencies can be selected to fall within a band of one or two VHF television channels (such as channels 12 and/or 13, which tend to have the lowest ambient noise), rather than spanning the entire 174 to 216 MHz range. It is estimated that such optimization will add a performance margin of 6 to 10 dB over existing telemetry equipment which operates over the entire 174 to 216 MHz range.

2. Communications Between Remote Telemeters and VCELLS (FIGS. 8–12)

Figure 8:
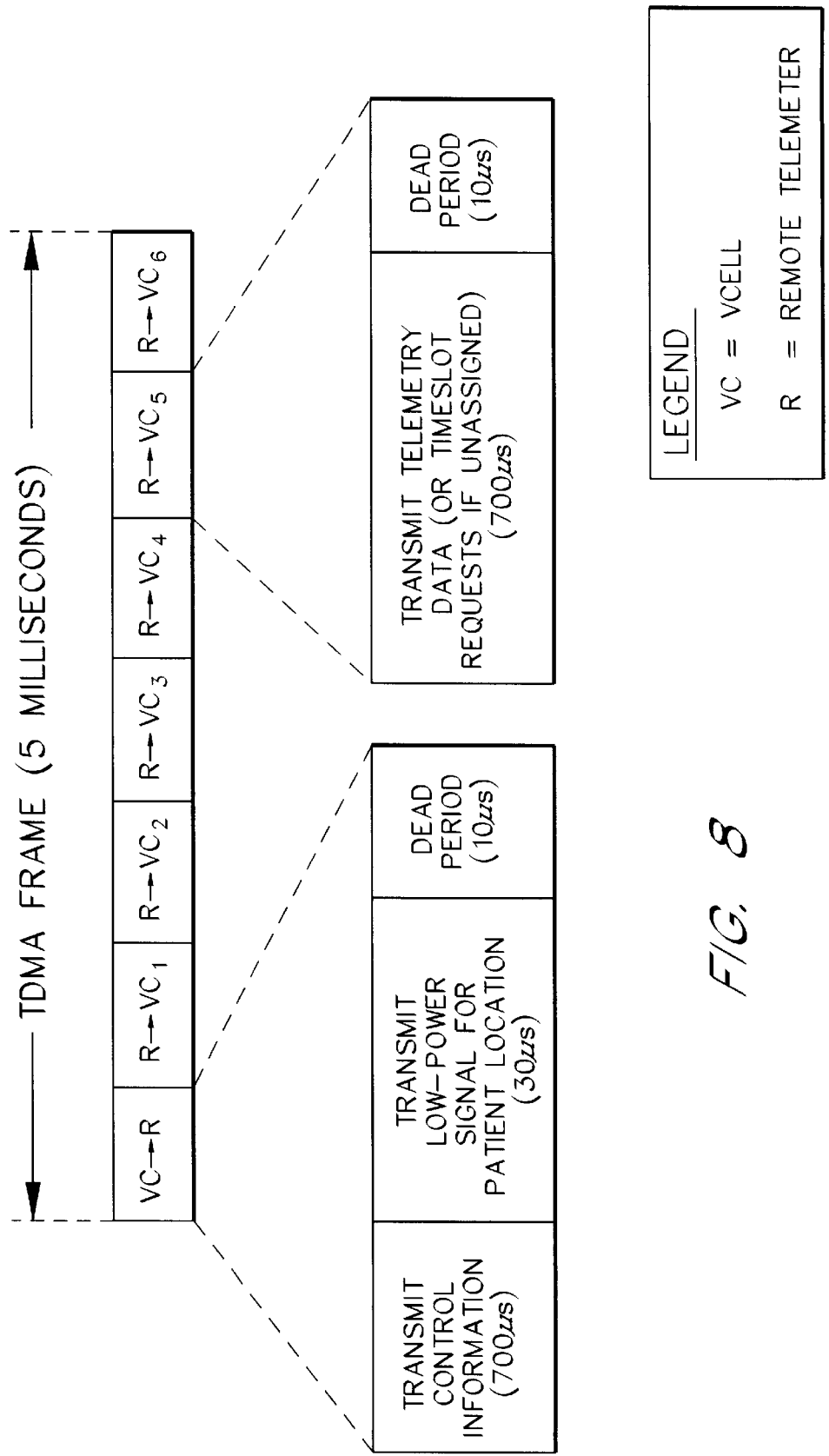
FIG. 8 illustrates a TDMA frame of a wireless TDMA protocol used for the transfer of information between the remote telemeters and the VCELLs of the system.

(i) Overall Wireless TDMA Protocol (FIG. 8)

FIG. 8 illustrates a single frame of the wireless TDMA protocol used between the remote telemeters 102 and the VCELLs 106. The frame repeats every 5 milliseconds, and consists of seven timeslots: a 740 microsecond ($\mu$s) VC→R (VCELL to remote telemeter) timeslot and six 710 $\mu$s R→VC (remote telemeter to VCELL) timeslots. The VC→R timeslots are used to broadcast information to the remote telemeters 102. (As described below, all VCELLs of the system are synchronized, and thus transmit at the same time.) The R→VC timeslots are assigned by the VCELLs 106 to individual telemeters 102, and are used to transfer information from the assigned telemeters to the VCELLs. All timeslots terminate with a 10 $\mu$s dead period, which is sufficient to allow the devices to switch between transmit and receive modes.

In the preferred embodiment, the remote telemeters 102 and VCELLs 106 transmit at a raw data rate of 80 Kbaud, which corresponds to a bit time of 12.5 $\mu$s. At this data rate, a total of (700 $\mu$s/slot)/(12.5 $\mu$s/bit)=56 bits are transmitted during the data portion of each R→VC timeslot. The first six of the 56 bit times are used for synchronization of the receiver, leaving 50 bits for the transfer of telemetry data (including error detection codes). Because this 50 bit message repeats every 5 milliseconds, or 200 times per second, the total telemeter-to-VCELL throughput for a single timeslot assignment is 200×50=10,000 bits/second, or 10 Kbaud. This throughput rate is obtained in the preferred embodiment using simple FM transceivers in the VCELLs and telemeters. As will be recognized by those skilled in the art, higher throughput rates can be achieved, at a greater expense, by using transceivers which use more sophisticated modulation techniques, such as BPSK and QPSK.

With further reference to FIG. 8, the VCELLs broadcast respective control messages to the remote telemeters 102 during the first 700 $\mu$s of each VC→R timeslot. (Because all VCELLs within range of one another transmit on different frequencies, each telemeter 102 can listen to the control message of only one VCELL at-a-time.) The control messages are used to transmit the following information to the telemeters:

Synchronization Sequences.

The telemeters use these sequences to initially become synchronized and to maintain synchronization with the VCELLs 106.

VCELL-Specific Timeslot Assignment Status Data.

For a given VCELL, this status data indicates which of the six R→VC timeslots (if any) are unassigned, and thus available for use. The telemeters use this information to formulate timeslot request messages to the VCELLs.

Telemeter-Specific Timeslot Assignment Messages.

A timeslot assignment message (or "confirmation" message) is transmitted in response to a timeslot request message from a specific telemeter, and serves as an acknowledgement to the telemeter that it has successfully acquired the requested timeslot.

Telemeter-Specific Commands.

This is an optional feature which may be supported by certain remote telemeters 102. A command may be sent, for example, to instruct a telemeter to take a blood pressure reading, or to enter into special mode of operation.

VCELL ID Codes.

Each VCELL transmits a unique ID code which is used for patient location.

During the last 30 $\mu$s of each VC→R timesiot, each VCELL transmits a low-power (¼-power in the preferred embodiment), unmodulated signal to allow each remote telemeter 102 to estimate the location of the respective patient. (The use of a low-power, unmodulated signal for this purpose produces a more accurate VCELL-telemeter distance measurement.) Each remote telemeter 102 measures the signal strengths of the low-power transmissions of the various VCELLs (by listening to different VCELL frequencies during different TDMA frames), and maintains a table (discussed below) of the detected signal strengths. As a low duty cycle task (e.g., once every 5 seconds), each telemeter 102 evaluates its respective table to estimate the closest VCELL (i.e., the VCELL with the greatest signal strength). Whenever a change occurs in the closest VCELL, the telemeter transmits the ID of the new VCELL to the hospital LAN 116 (FIG. 1). The monitoring stations 120 use this information to keep track of the locations of the patients of the system. In other embodiments of the invention, patient location may be accomplished by having the VCELLs periodically attach VCELL identification codes to the data packets received from the remote telemeters 102.

With further reference to FIG. 8, the six R→VC timeslots are used by the remote telemeters 102 to transmit data packets to individual VCELLs 106. (As described below, each telemeter 102 transmits to only one VCELL at-a-time.) These data packets are generally of two types: (i) telemetry data packets which include the patient data (including patient location data) of individual patients, and (ii) timeslot request messages for requesting timeslot assignments. Once a R→VC timeslot has been assigned by a VCELL to a remote telemeter, the remote telemeter has exclusive use of the timeslot until the telemeter disconnects. Once the telemeter disconnects, the VCELL modifies its control message (transmitted on the VC→R timeslot) to indicate that the timeslot is available for use.

During normal operation, each R→VC timeslot of a given VCELL 106 will be assigned, if at all, to a different remote telemeter 102. Thus, when all six R→VC timeslots of the VCELL are assigned, the VCELL receives the telemetry data of six different remote telemeters 102. In other modes of operation, multiple timeslots of a single VCELL can be assigned to the same telemeter to allow the telemeter to achieve a higher data throughput rate.

Figure 10:
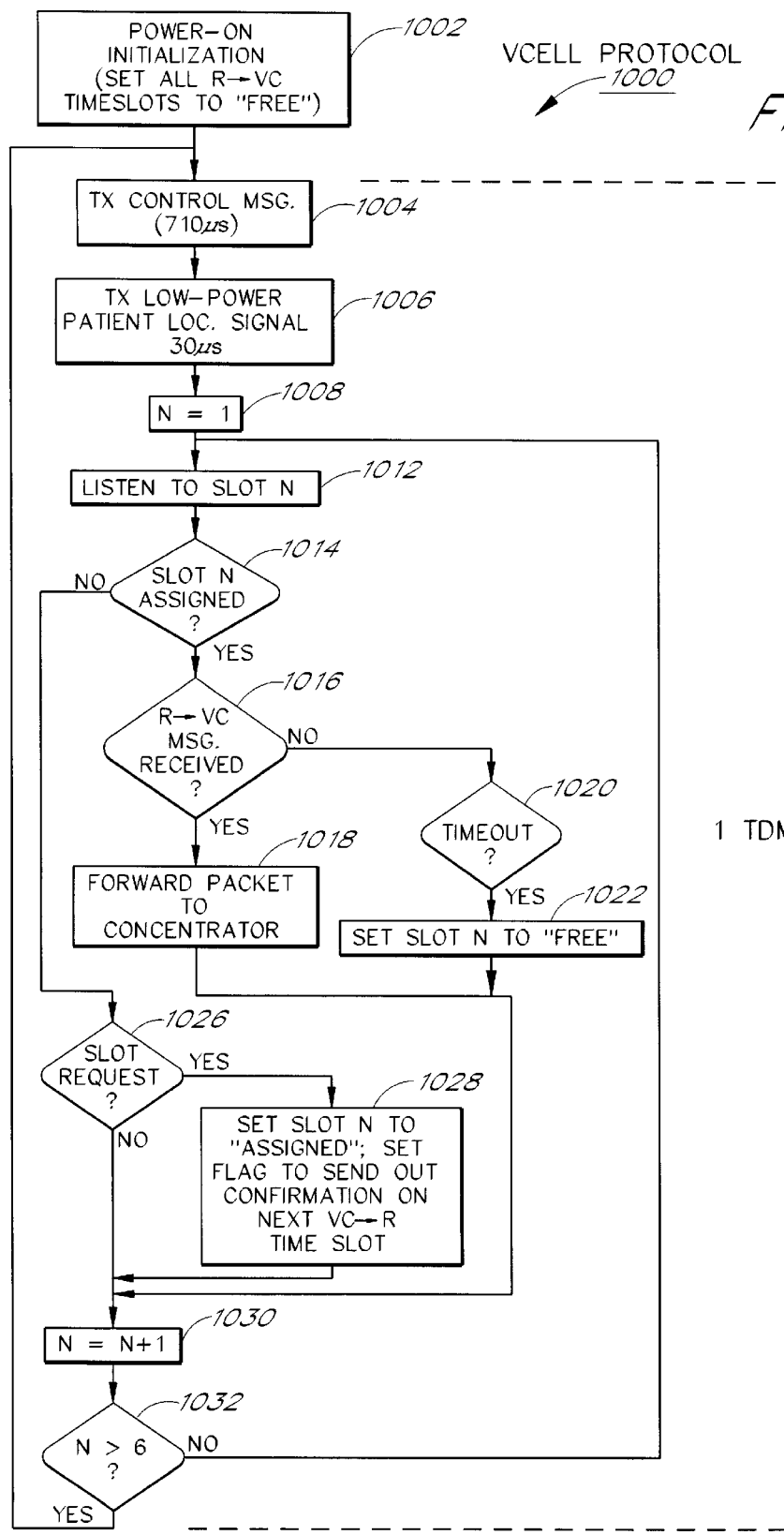
FIG. 10 is a flowchart of a protocol followed by each VCELL as part of the wireless TDMA protocol.

(ii) VCELL Protocol (FIGS. 9 and 10)

The VCELL side of the above-described wireless TDMA protocol is implemented via a firmware program which is executed by the microcontroller of each VCELL 106. With reference to FIG. 9, this program maintains a timeslot status table 900 in VCELL RAM 310 to keep track of the assignment status of each R→VC timeslot. As illustrated in FIG. 9, the information stored within the table 900 includes, for each timeslot, whether or not the timeslot is currently assigned or unassigned. In addition, for the timeslots that are assigned, the table indicates the number of consecutive frames that have passed without receiving an error-free data packet from the assigned telemeter; each VCELL uses this information to implement a timeout procedure to determine whether the assigned telemeter 102 has disconnected.

FIG. 10 is a flow chart which illustrates the VCELL portion of the wireless protocol. With reference to block 1002, during a power-on initialization sequence, the VCELL 106 updates its timeslot status table 900 to set all of the R→VC timeslots to the "free" (unassigned) state. The VCELL then enters into a primary program loop which corresponds to a single TDMA frame. Referring to blocks 1004 and 1006 of this loop, during the VC→R timeslot the VCELL transmits the 710 μs control message followed by the 30 μs patient location signal, as illustrated in FIG. 8. This control message includes the timeslot assignment data (for all six R→VC slots) stored in the timeslot status table 900. On the first pass through this loop following power-on, the control message will indicate that all six R→VC timeslots are available for use. With reference to block 1008, the VCELL 106 then sets a slot counter (N) to one (corresponding to the first R→VC timeslot), and enters into a sub-loop (blocks 1012–1032) for processing the data packets transmitted by the telemeters.

During each R→VC timeslot, the VCELL attempts to receive any telemeter data packet transmitted during the timeslot (block 1012), and checks the timeslot status table 900 to determine whether the slot is assigned (block 1014). With reference to blocks 1016–1022, if the timeslot is assigned and a data packet was successfully received, the VCELL forwards the packet to the concentrator 112, and clears the corresponding "missed packets" counter in the status table 900. (The data packet is actually sent to the concentrator 112 following the TDMA frame as part of a larger "VCELL packet" which represents the entire frame.) If, on the other hand, the timeslot is assigned but no packet was successfully received, the VCELL 106 updates the timeslot status table 900 to indicate that a packet was missed; in addition, the VCELL determines whether the number of consecutive missed packets has exceeded a timeout threshold (e.g., 64 packets). If the threshold is exceeded, the status table 900 is updated to set the timeslot to the "free" state.

With reference to blocks 1026 and 1028, if the timeslot is unassigned, the VCELL 106 determines whether it received a valid timeslot request message. If a valid timeslot request was received, the VCELL updates its status table to indicate that the slot has been assigned; in addition, the VCELL sets a flag to indicate that a timeslot confirmation message should be transmitted to the requesting telemeter 102 during the next VC→R timeslot.

With reference to blocks 1030 and 1032, once all processing of the received telemeter packet (if any) is performed, the VCELL increments its timeslot counter. If the incremented counter is 6 or less, the program loops back to block 1012 to begin receiving any data transmitted during the next timeslot. If the incremented counter has exceeded 6, the program loops back to block 1004 to transmit the next control message.

Although the FIG. 10 flowchart illustrates the above-described operations in sequential order, it will be recognized that some of these operations can (and normally will) be performed concurrently or out-of order. For example, the step of forwarding the data packets to the concentrator (block 1018) is preferably performed as a separate task, with all of the telemeter packets received during the TDMA frame transferred together within a larger VCELL packet.

Figure 12:
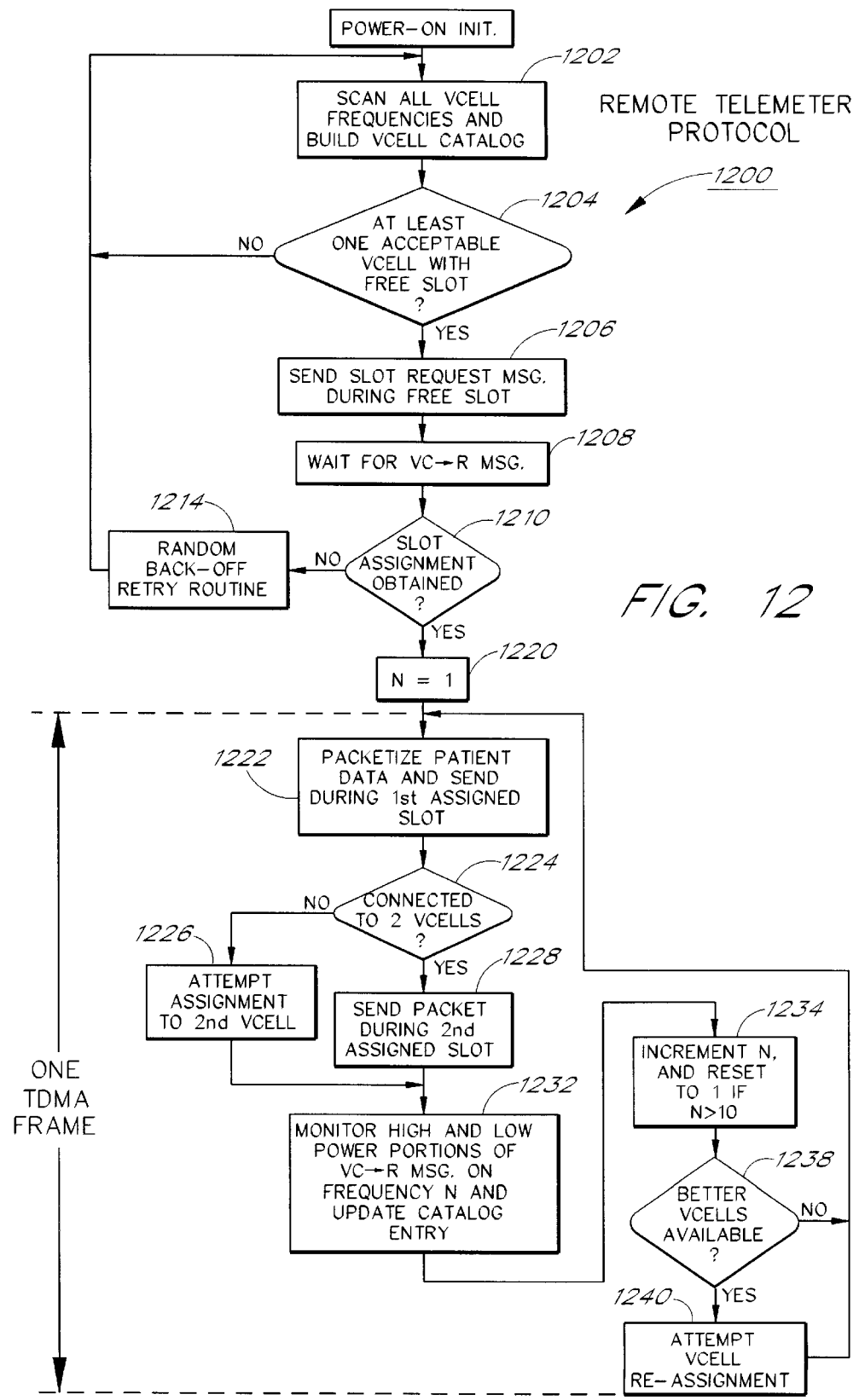
FIG. 12 is a flowchart of a protocol followed by each remote telemeter as part of the wireless TDMA protocol.

(iii) Remote Telemeter Protocol (FIGS. 11 and 12)

The telemeter side of the wireless TDMA protocol generally mirrors the VCELL protocol 1000, and is similarly implemented by a firmware program which is executed by the microcontroller of each remote telemeter 102. As part of this protocol, each remote telemeter 102 maintains a VCELL catalog within its respective RAM 406. The general format of this catalog is illustrated in FIG. 11, which is representative of a system which uses a total of 10 VCELL frequencies. As illustrated in FIG. 11, the catalog 1100 includes one set of entries for each of the ten VCELL frequencies. The telemeter thus stores status information for up to ten nearby VCELLs at-a-time. The entries stored with respect to each VCELL frequency include the following:

Rating.

A rating of the quality of the RF link to the VCELL 106, as assessed by the individual telemeter 102. The RF links are assessed by the telemeters one frequency at-a-time during the control message portions of the VC→R timeslots. (In other embodiments, the task of assessing the available RF links may alternatively be performed by the VCELLs.) In one embodiment, the VCELL ratings are based on a combination of signal strength (as measured by the telemeters) and bit error rate. Specifically, if an error is detected in a VCELL's transmission, the VCELL's rating is set to a zero or null entry to indicate that the VCELL should not be used; and if no error is detected, the rating is set to a value which is proportional to the measured signal strength. The ratings are periodically compared (as described below) to determine whether to attempt a connection to a new VCELL.

Connected To.

A flag indicating whether or not the telemeter is connected to a VCELL on the frequency. During normal operation, each telemeter will be connected to two different VCELLs (on two different frequencies) at-a-time.

Low-Power Signal Strength.

A measurement of the signal strength taken during the low-power (patient location) portion of the VC→R timeslot. The low-power signal strengths stored in the catalog 1100 are periodically compared to estimate which of the VCELLs the patient is closest to. When the outcome of this comparison changes, the telemeter transmits the new location (i.e., the VCELL ID, which is obtained from the VCELL during the high-power message portion) to the hospital LAN 116 in a subsequent data packet.

The remote telemeters 102 also keep track of the unique IDs of the VCELLs that are within range.

The protocol followed by the remote telemeters 102 generally consists of the following steps:

1. Scan all VCELL operating frequencies and construct the VCELL catalog 1100. Remain in this mode until at least one VCELL 106 is identified which has an acceptable rating and an unassigned timeslot.
2. Send a timeslot request message to the VCELL identified in step 1 during one of the available timeslots. Perform this task using a random back-off algorithm in case other remote telemeters attempt to connect to the VCELL during the same timeslot. Remain in this operating mode (including step 1) until a timeslot assignment message is received from the selected VCELL.
3. Once connected to a first VCELL ("VCELL 1"), attempt to connect to the "next best" VCELL ("VCELL 2") in the catalog which has an acceptable rating and a free timeslot (other than the timeslot being used to communicate with VCELL1), to provide a second (diversity) data path. Send telemetry data packets to VCELL1 during this process.
4. Monitor the catalog entries to determine whether any of the other VCELLs offer better link performance than VCELLs 1 and 2. When a better VCELL is available (i.e., has an open, nonconflicting timeslot), send a timeslot request message to the "new" VCELL. Drop the connection with the current VCELL once a timeslot assignment message is received.
5. As a background task, scan the VCELL frequencies and update the catalog. This can be done as a low priority, low duty cycle task (such as once per second).

FIG. 12 illustrates this protocol in greater detail for a system which uses 10 VCELL frequencies. With reference to block 1202, the remote telemeter 102 initially scans the ten VCELL frequencies and builds the VCELL catalog 1100. This involves monitoring different VCELL frequencies during different TDMA frames. With reference to blocks 1204–1210, once an acceptable VCELL 106 with an open timeslot has been identified, the telemeter 102 transmits a timeslot request message to the selected VCELL, and then monitors the selected VCELL's frequency during the following VC→R timeslot to determine whether the slot has been successfully acquired. With reference to block 1214, if the connection attempt is unsuccessful, a random back-off algorithm (such as the binary exponential back-off algorithm used by Ethernet) is used to retry the connection attempt. If the retry is unsuccessful (after, for example, 2 retry attempts), or if it is determined that the requested timeslot has been assigned to a different telemeter 102, the telemeter repeats the above process to identify another potential VCELL.

With reference to blocks 1220–1226, once a timeslot assignment has been obtained from a first VCELL, the protocol enters into a loop (blocks 1222–1240) which corresponds to a single TDMA frame. Within this loop, the telemeter 102 sends telemetry data packets to the first VCELL (block 1222) during the assigned timeslot while attempting to connect to a second VCELL (block 1226). The process of connecting to the second VCELL is generally the same as the above-described process for connecting to the first VCELL, with the exception that the timeslot used to communicate with the second VCELL must be different from the timeslot used to communicate with the first VCELL. With reference to block 1228, once a second VCELL connection has been established, the telemeter sends all data packets to both VCELLs.

With reference to blocks 1232 and 1234, the remote telemeter 102 monitors the high-power and low-power transmissions of the VCELLS 106 (during the VC→R timeslots) and updates the rating and low-power signal strength entries of the VCELL catalog 1100. Although this process is shown in FIG. 12 as occurring during every TDMA frame (one VCELL per frame), this function can alternatively be performed as a low duty cycle task.

With reference to blocks 1238 and 1240, as a background task the telemeter 102 monitors the VCELL catalog 1100 to determine whether a VCELL 106 with a higher rating exists. If a VCELL with a higher rating and an available (nonconflicting) timeslot is identified, the telemeter attempts to connect to the new VCELL (as described above), and if successful, drops the existing connection to one of the two "current" VCELLs.

As a background, low priority task, the telemeter 102 also monitors the VCELL catalog 1100 to determine whether a change has occurred in the VCELL 106 with the greatest low-power signal strength. (This process is omitted from FIG. 12 to simplify the drawing.) When such a change occurs, the telemeter transmits the VCELL ID of the new "closest" VCELL in a subsequent telemetry packet. As described above, this information is used by the monitoring stations 120 to track the location of each patient.

3. Communications Between VCELLs and Concentrators (FIG. 13)

The VCELLs 106 and concentrators 112 communicate bi-directionally over the shielded twisted pair lines 110 in accordance with the RS-422 specification. (RS-422 is an Electronic Industries Association interface standard which defines the physical, electronic and functional characteristics of an interface line which connects a computer to communications equipment.) The RS-422 interface supports an overall data transfer rate of 140 Kbaud, which corresponds to 20 Kbaud per TDMA timeslot.

In operation, each VCELL 106 sends one packet to its respective concentrator 112 for every TDMA frame; this VCELL packet includes all of the telemeter packets (up to six) received during the corresponding TDMA frame. (The terms "VCELL packet" and "telemeter packet" are used in this description to distinguish between the two types of packets based on their respective sources.) The concentrator 112 in-turn parses the VCELL packet to extract the individual telemeter packets, and performs error checking on the telemeter packets using the error detection codes contained within such packets. As part of the error checking protocol, the concentrator 112 discards all telemeter packets which include errors (or uncorrectable errors if error correction codes are used), and discards all telemeter packets that are redundant of packets already received from a different VCELL. All other packets are written to an output buffer for subsequent broadcasting over the LAN 116.

FIG. 13 is a flow chart which illustrates the concentrator side of the VCELL-to-concentrator protocol in further detail. With reference to block 1302, the concentrator 112 sends a VCELL synchronization pulse to its 16 VCELLs once per TDMA frame. The concentrator then initializes a loop counter (block 1304), and enters into a loop (blocks 1306–1324) in which the concentrator processes the 16 VCELL packets (one per loop) received from the 16 VCELLs. Within this loop, the concentrator 112 parses each VCELL packet (block 1306) to extract the individual telemeter packets contained therein, and then enters into a sub-loop (blocks 1310–1320) in which the concentrator performs error checking (as described above) on the individual telemeter packets (one telemeter packet per sub-loop).

With reference to blocks 1310–1316, error free telemeter packets which have not already been successfully received (from other VCELLs) are written to an output buffer of the concentrator 112. (As described below, a separate concentrator task reads these packets from the buffer and broadcasts the packets on the LAN 116 during patient-specific timeslots of the LAN protocol.) With reference to blocks 1320–1324, once all of the telemeter packets within a given VCELL packet have been processed, the protocol loops back to block 1306 (unless all 16 VCELL packets have been processed, in which case a new synchronization pulse is transmitted), and the concentrator 112 begins to process the next VCELL packet.

As indicated by the foregoing, the concentrators 112 only place error-free telemeter packets on the LAN backbone 118, and do not place duplicate error-free telemeter packets (from the same telemeter) on the backbone 118. Nevertheless, the duplicate (error-free) packets transmitted by a telemeter will normally appear on the LAN backbone 118 when the remote telemeter connects to VCELLs of two different concentrators 112 (as permitted in one implementation of the invention). In this situation, the monitoring stations 120 simply ignore the extra telemeter packets.

(i) Processing of Telemeter Commands

In system implementations which support the sending of commands to the remote telemeters 102, the concentrators 112 additionally implement a simple task (not illustrated in FIG. 13) for receiving commands from the monitoring stations 120 and forwarding these commands to the VCELLs 106. As part of this task, each concentrator 112 maintains a list of all of the remote telemeters 102 to which the concentrator is currently connected. (This list is generated by monitoring the telemeter ID codes contained within the telemeter data packets.) When a monitoring station 120 places a telemeter-addressed command on the LAN 116, each concentrator 112 of the system receives the command and checks its respective list to determine whether a connection exists with the target telemeter. If a concentrator determines that such a connection currently exists, the concentrator 112 sends the command to all 16 of its VCELLs 106. The sixteen VCELLs in-turn transmit the telemeter command during a subsequent VC→R timeslot. To increase the probability of receipt, the VCELLs are preferably configured to re-transmit the telemeter command over several TDMA frames. In other embodiments, an acknowledgement protocol can be implemented in which the telemeters embed an acknowledgement message within a subsequent data packet.

4. Data Transfers Over LAN

Data transfers over the LAN backbone 118 are accomplished using a real-time TDM (time division multiplexing) protocol which makes use of the 100BaseTx protocol. Among other things, this protocol distributes the telemetry data from the concentrators 112 to the monitoring stations 120 with a known latency, permitting the real-time monitoring of patient data.

Each 50 millisecond frame of the TDM protocol includes 1000, 50 µs timeslots. Every remote telemeter 102, VCELL 106, concentrator 112, monitoring station 120, and gateway 124 of the system is uniquely assigned one of the 1000 backbone timeslots. The backbone timeslots that are uniquely assigned to respective remote telemeters 102 are used to transfer telemetry data packets (containing patient-specific physiologic data) from the concentrators 112 to the monitoring stations 112. All other entities that are connected to the LAN backbone 118 also have access to this telemetry data. The remaining backbone timeslots are used for the transfer of synchronization and control information between the various LAN entities.

The 100BaseTx backbone 118 has the capacity to transfer up to 5000 bits in each 50 µs backbone timeslot. Thus, each remote telemeter (and other entity which is assigned a backbone timeslot) is effectively allocated a LAN bandwidth of 5000 bits/slot×20 frames/second=100 Kbaud. This more than satisfies the 20 Kbaud data rate per telemeter which is required when a telemeter connects to VCELLs of two different concentrators.

Upon initialization of the system, a "master" concentrator 112 transmits a synchronization packet to all other concentrators of the LAN 116. This synchronization packet defines the starting point of the backbone TDM frame. Thereafter, the frame repeats at a rate of 20 frames per second. As indicated above, a task which runs on each concentrator moves telemeter packets from the concentrator's output buffer to the LAN during the appropriate patient-specific (50 µs) timeslots. This task waits for a patient (telemeter) timeslot, and then transmits all corresponding telemeter packets which have been written to the output buffer since the same timeslot of the immediately preceding backbone frame. When a telemeter is connected to VCELLs of two different concentrators, the 50 µs patient timeslot is divided equally between the two concentrators. This is accomplished by passing control messages between the concentrators.

5. VCELL Load Monitoring

As a background task, each concentrator 112 maintains a statistical log or "histogram" of the loads carried by each of the concentrator's VCELLs 106. This histogram can periodically be examined by network administrators to evaluate the current positioning of the VCELLs. When, for example, the histogram indicates that a VCELL in a particular patient area reaches its capacity (i.e., all six timeslots assigned) on a frequent basis, another VCELL (which operates on a different frequency) can be installed in the area to reduce the load on the heavily-loaded VCELL.

6. Transceiver Circuit and Operation (FIGS. 5A and 5B) The transceiver circuit illustrated in FIG. 5A will now be described. As indicated above, this general circuit can be used in both the remote telemeters 102 and the VCELLs 106 of the system. When included within a remote telemeter 102, the transceiver will typically be powered by battery. When included within a VCELL 106, the transceiver will be powered by the corresponding concentrator 112 over a twisted pair line 110 (as illustrated in FIG. 3).

The transceiver 112 comprises a microcontroller (preferably a 17C42) which is connected, via appropriate port lines, to a programmable phase-locked loop chip 504 ("PLL chip"), a voltage controlled oscillator (VCO) 506, a receiver (RCVR) 508, a set of DIP (dual in-line package) switches 510, an EEPROM 512, and a sample-and-hold (S/H) device 520. (The sample-and-hold 520 is preferably omitted in the VCELL transceivers 308.) The PLL chip 504 is preferably a Motorola MC 145192 which can be placed, via appropriate commands, into a low-power state when not in use. The microcontroller 502 is clocked by an 8 MHz high stability (±0.001 %) crystal oscillator 516. The output of the amplifier 524 and the signal input of the receiver 508 are connected to respective terminals of a transmit/receive switch 528, which is connected to the antenna 312, 408 via a band-pass filter (BPF) 530.

As illustrated in FIG. 5A, the PLL chip 504 is coupled to the VCO 506 to form a phase lock loop circuit. Via the PLL chip 504, the phase lock loop circuit can be programmed to generate a carrier signal of a selected frequency. Within the transceivers of the telemeters 102, the sample-and-hold device 520 is connected so as to allow the microcontroller 502 to programmably interrupt the phase-lock process and hold the carrier frequency at a steady frequency value within a preselected margin of frequency error. This allows the carrier frequency to be locked rapidly, at low power, without waiting for a phased-locked state to be reached. In a preferred embodiment, this feature is used to lock the transmit frequency of each telemeter just prior to each R→VC timeslot to which the telemeter is assigned.

As illustrated in FIG. 5A, the VCO 506, amplifier 524, and receiver 508 are coupled to the power supply ($V_{SUP}$) via respective microcontroller-controlled switches 534, 536, 538 such that the microcontroller 502 can selectively turn these components ON and OFF to conserve power. (In the VCELLs, the switches 534, 536, 538 can be omitted since battery life is not a concern.) To utilize this power-conservation feature, the firmware program (stored within the EEPROM 512) of the remote telemeters 102 includes code for maintaining these active transceiver components in an OFF state when not in use. For example, the receiver is maintained in an OFF state during TDMA timeslots for which the remote telemeter 102 is not receiving data, and the amplifier is maintained in an OFF state during timeslots for which the remote telemeter 102 is not transmitting. This feature of the transceiver circuit significantly increases the average battery life of the remote telemeters 102.

In operation within a remote telemeter, the microcontroller 502 maintains the PLL chip 504 in its low-power state, and maintains the amplifier 424, VCO 506 and receiver 508 in respective OFF states, during timeslots for which the telemeter is neither transmitting nor receiving data. Shortly before the next R→VC timeslot which is assigned to the telemeter 102, the microcontroller 502 initiates a frequency lock operation which involves initiating a phase-lock process, and then interrupting the process (by opening the sample-and-hold 520) once the carrier frequency has settled to within an acceptable margin of error. This process is illustrated in Figure 5B, which is an approximate graph of the output ($V_{PLL}$) of the PLL chip 504 following power-up at $T_0$.

With reference to FIG. 5B, just prior to $T_0$, the VCO 506 is turned on, the sample-and-hold 520 is in the closed (or "sample") position, and the PLL chip 504 is in the low-power state. At $T_0$, the PLL chip 504 is taken out of the low-power state, causing its output $V_{PLL}$ to ring, and thus causing the output of the VCO to oscillate above and below the programmed transmit frequency. Following $T_0$, the output of the PLL is in the general form of a damped sinusoid, which approaches the voltage that corresponds to the programmed frequency. (Because the voltage $V_{PLL}$ controls the VCO 506, the amplitude of the voltage signal in FIG. 5B corresponds to the frequency.) Once this oscillation is sufficiently attenuated such that the frequency error is within a predetermined tolerance (e.g., ±5 KHz), the sample-and-hold 520 is opened (at $T_1$ in FIG. 5) to hold the input voltage to the VCO 506. (This is accomplished by waiting a predetermined delay, $T_{DELAY}$, before opening the sample-and hold 520, as described in the above-referenced priority application.) This holds the output frequency, and ensures that the remote telemeter's subsequent data transmission will not be contaminated by any oscillation in the PLL's output. Immediately following T1, the amplifier 524 is turned on, the PLL 504 is placed in the low-power state, and the T/R switch 528 is placed in the transmit position. The microcontroller 402 then begins sending its transmit data to the VCO, to thereby FSK-modulate the carrier signal. Following the transmission of the telemeter packet, the amplifier 524, and VCO 506 are turned off.

In one embodiment, the telemeter firmware is written such that the telemeters 102 only use non-adjacent (i.e., non-consecutive) R→VC timeslots. This ensures that each telemeter will have at least a 720 $\mu s$ "dead period" between transmissions during which to lock the new transmit frequency using the above-described process.

The process of receiving data (during VC→R timeslots) is generally analogous to the above-described transmit process, with the exception that the sample-and-hold 520 is left in the closed (sample) position throughout the VC→R timeslot.

7. Conclusion

While the present invention has been described herein with reference to a preferred embodiment of a medical telemetry system, the invention is not so limited, and should be defined only in accordance with the following claims.

What is claimed is:

1. A medical telemetry system for permitting real-time monitoring of patients, including ambulatory patients, of a medical facility from a centralized monitoring station, comprising:

at least one monitoring station which displays real-time physiologic data of multiple patients;

a plurality of battery-powered wireless remote telemeters, the remote telemeters configured to attach to, and configured to collect and transmit real-time physiologic data of, respective patients; and a plurality of transceivers which communicate bi-directionally with the plurality of remote telemeters using a plurality of wireless radio frequency (RF) channels, the transceivers connected to the at least one monitoring station and being distributed throughout the medical facility such that different transceivers provide data-reception coverage for different areas of the medical facility, at least some of the transceivers receiving physiologic data on different RF channels, the transceivers configured to receive the physiologic data transmitted by the remote telemeters and to forward the physiologic data over a wired connection to the at least one monitoring station;

wherein at least some of the remote telemeters automatically switch between different RF channels of the plurality of RF channels in response to patient movement throughout the medical facility to connect to and disconnect from individual transceivers of the plurality of transceivers.

2. The medical telemetry system according to claim 1, wherein at least some of the remote telemeters evaluate wireless link conditions offered by different transceivers and establish wireless connections with individual transceivers based at least upon said wireless link conditions.

3. The medical telemetry system according to claim 2, wherein at least one remote telemeter of the plurality of remote telemeters maintains wireless connections with at least two different transceivers at-a-time, and transmits the physiologic data of a respective patient to the at least two different transceivers to provide at least spacial diversity.

4. The medical telemetry system according to claim 2, wherein the remote telemeters communicate with the transceivers using a TDMA protocol, and the at least one remote telemeter transmits the physiologic data to the at least two different transceivers during different respective TDMA timeslots to thereby additionally provide time diversity.

5. The medical telemetry system according to claim 4, wherein the at least one remote telemeter transmits the physiologic data to the at least two different transceivers on different RF frequencies, the different RF frequencies spaced sufficiently apart to provide frequency diversity.

6. The medical telemetry system according to claim 1, wherein the transceivers forward the physiologic data to the at least one monitoring station over a local area network.

7. The medical telemetry system according to claim 1, wherein at least two of the transceivers communicate with the remote telemeters on the same RF channel.

8. The medical telemetry system according to claim 7, wherein the at least two transceivers which communicate on the same RF channel are sufficiently spaced apart to avoid interference with one another.

9. The medical telemetry system according to claim 1, wherein at least some of the transceivers of the plurality of transceivers are synchronized with one another.

10. The medical telemetry system according to claim 1, wherein different subsets of the plurality of transceivers are connected to respective concentrator computers, each concentrator computer receiving physiologic data from a respective subset of transceivers and forwarding the physiologic data to the at least one monitoring station.

11. The medical telemetry system according to claim 10, wherein the concentrator computers are interconnected by a local area network.

12. The medical telemetry system according to claim 11, wherein the local area network comprises a plurality of monitoring stations which display the real-time physiologic data of the patients.

13. The medical telemetry system according to claim 1, wherein the remote telemeters communicate with the transceivers using a TDMA protocol, and at least one of the transceivers broadcasts timeslot availability messages to the remote telemeters, the timeslot availability messages indicating available and unavailable TDMA timeslots for communicating with the at least one transceiver.

14. The medical telemetry system according to claim 13, wherein different transceivers of the plurality broadcast timeslot availability messages to the remote telemeters on different RF frequencies.

15. The medical telemetry system according to claim 1, wherein the plurality of transceivers communicate with the plurality of remote telemeters within a VHF medical telemetry band.

16. The medical telemetry system according to claim 1, wherein at least one of the remote transceivers maintains wireless connections with multiple remote telemeters at-a-time.

17. The medical telemetry system according to claim 1, wherein at least one of the remote transceivers is positioned proximate to a known intermittent source of electromagnetic interference.

18. The medical telemetry system according to claim 17, wherein the at least one remote transceiver is positioned within a patient X-ray room.

19. The medical telemetry system according to claim 1, wherein at least some of the transceivers transmit patient location signals to the remote telemeters.

20. The medical telemetry system according to claim 1, wherein at least one remote telemeter of the plurality of remote telemeters includes a processor which executes a control program to implement a wireless communications protocol in which the remote telemeter transmits data packets to different transceivers during different timeslots, the control program configured to maintain wireless connections with at least two different transceivers at-a-time on at least two different RF channels, and to transmit data packets that contain like physiologic data to the at least two different transceivers to provide multiple simultaneous transmission paths for the transfer of the physiologic data between the remote telemeter and the monitoring station.

21. A method of transferring real-time physiologic data of a patient from a wireless remote telemeter to a receiving node of a network so as to provide protection against multi-path interference, the remote telemeter configured to attach to the patient, the method comprising:

providing first and second transceivers that are positioned within respective first and second patient areas of a medical facility, the patient areas being sufficiently close to one another so that the transceivers provide overlapping first and second coverage zones, each transceiver positioned remotely from and being connected to the receiving node;

transmitting a first data packet from the remote telemeter to the first transceiver during a first timeslot, the first data packet containing at least the real-time physiologic data;

transmitting a second data packet from the remote telemeter to the second transceiver during a second timeslot which is different from the first timeslot, the second data packet containing at least the real-time physiologic data;

forwarding the first and second data packets, respectively, from the first and second transceivers to the receiving node; and selecting between the first and second data packets at the receiving node.

22. The method according to claim 21, wherein the first and second data packets contain respective error detection codes, and the step of selecting comprises evaluating the error detection codes at the receiving node to determine whether the first and second data packets were successfully received by the first and second transceivers.

23. The method according to claim 22, wherein the error detection codes comprise error correction codes.

24. The method according to claim 21, wherein the step of transmitting the first data packet is performed on a first frequency channel and the step of transmitting the second data packet is performed on a second frequency channel, the first and second frequency channels sufficiently different to provide frequency diversity.

25. The method according to claim 24, wherein the first and second frequency channels fall within a VHF medical telemetry band.

26. The method according to claim 21, further comprising sending either the first data packet or the second data packet from the receiving node to a patient monitoring station over a wired local area network.

27. The method according to claim 21, wherein the step of forwarding the first and second data packets to the receiving node comprises transmitting the packets over different respective wired connections.

28. The method according to claim 21, wherein the steps of transmitting first and second packets from the remote telemeter are repeated periodically to transmit the patient's ECG waveform data in real-time to the receiving node.

29. The method according to claim 21, further comprising:

positioning a third transceiver within a third patient area to provide a third coverage zone which overlaps with the first and second coverage zones, the third transceiver positioned remotely from and being connected to the receiving node; and in response to patient movement away from the first patient area towards the third patient area, automatically establishing a connection between the remote telemeter and the third transceiver and terminating a connection between the remote telemeter and the first transceiver.

30. The method according to claim 29, wherein the step of establishing a connection with the third transceiver comprises sending a timeslot request message from the remote telemeter to the third transceiver.

31. The method according to claim 29, wherein the step of establishing a connection with the third transceiver comprises:

broadcasting a timeslot availability message from the third transceiver, the timeslot availability message indicating available and unavailable timeslots for communicating with the third transceiver; and receiving the timeslot availability message with the remote telemeter, and evaluating the timeslot availability message to identify an available timeslot.

32. The method according to claim 29, wherein the first, second and third transceivers communicate with the remote telemeter on different respective frequency channels.

33. A medical telemetry system for monitoring patients of a medical facility, the system comprising:

a plurality of transceivers distributed throughout the medical facility such that different transceivers provide data reception coverage for different areas of the medical facility, the plurality of transceivers connected to a common data receiving node, at least some of the transceivers of the plurality operating on different radio frequency (RF) channels; and a wireless remote telemeter that is configured to be worn by an ambulatory patient, the remote telemeter including sensing circuitry for sensing physiologic data of the patient, the remote telemeter implementing a wireless communications protocol in which the remote telemeter transmits data packets to different transceivers of the plurality during different timeslots, and in which the remote telemeter maintains wireless connections with at least two different transceivers at-a-time on at least two different RF channels and transmits like physiologic data to the at least two different transceivers to provide multiple concurrent transmission paths for the transfer of the physiologic data from the remote telemeter to the receiving node.

34. The medical telemetry system according to claim 33, wherein the remote telemeter implements a switch-over protocol in which the remote telemeter automatically connects to and disconnects from different transceivers of the plurality based on assessments of RF link conditions.

35. The medical telemetry system according to claim 33, wherein the physiologic data comprises ECG waveform data, and the remote telemeter transmits the ECG waveform data to the at least two different transceivers in real-time.

36. The medical telemetry system according to claim 32, wherein each transceiver is configured to concurrently receive the physiologic data of multiple patients from multiple telemeters.

* * * * *